United States Patent
Jiang et al.

(10) Patent No.: US 12,012,453 B2
(45) Date of Patent: Jun. 18, 2024

(54) METHODS FOR TREATING LATE-STAGE SMALL CELL LUNG CANCER BY ADMINISTERING A HUMAN ANTI-PD-L1 ANTIBODY, AN ETOPOSIDE AND A PLATINUM-BASED THERAPEUTIC

(71) Applicant: ASTRAZENECA AB, Sodertalje (SE)

(72) Inventors: Haiyi Jiang, Gaithersburg, MD (US); Yifan Huang, Gaithersburg, MD (US); Phillip Dennis, Gaithersburg, MD (US); Norah Shire, Gaithersburg, MD (US); Jon Armstrong, Cambridge (GB)

(73) Assignee: ASTRAZENECA AB, Sodertalje (SE)

(*) Notice: Subject to any disclaimer, the term of this patent is extended or adjusted under 35 U.S.C. 154(b) by 95 days.

(21) Appl. No.: 17/012,643

(22) Filed: Sep. 4, 2020

(65) Prior Publication Data

US 2021/0070863 A1 Mar. 11, 2021

Related U.S. Application Data

(60) Provisional application No. 62/896,224, filed on Sep. 5, 2019.

(51) Int. Cl.
| | |
|---|---|
| C07K 16/28 | (2006.01) |
| A61K 9/00 | (2006.01) |
| A61K 31/555 | (2006.01) |
| A61K 31/7048 | (2006.01) |
| A61K 33/243 | (2019.01) |
| A61P 35/00 | (2006.01) |

(52) U.S. Cl.
CPC ........ *C07K 16/2827* (2013.01); *A61K 9/0019* (2013.01); *A61K 31/555* (2013.01); *A61K 31/7048* (2013.01); *A61K 33/243* (2019.01); *A61P 35/00* (2018.01); *C07K 16/2818* (2013.01)

(58) Field of Classification Search
CPC ............ C07K 16/2827; C07K 16/2818; A61K 9/0019; A61K 31/555; A61K 33/243; A61P 35/00
See application file for complete search history.

(56) References Cited

U.S. PATENT DOCUMENTS

| | | | |
|---|---|---|---|
| 8,491,895 | B2 | 7/2013 | Hanson et al. |
| 8,779,108 | B2 | 7/2014 | Queva et al. |
| 9,493,565 | B2 | 11/2016 | Queva et al. |
| 2020/0030443 | A1* | 1/2020 | Lopez-Chavez ..... A61K 31/136 |

OTHER PUBLICATIONS

Hamid et al. Combination of MEDI0680, an anti-PD-1 antibody with Durvalumab, an anti-PD-L1 antibody: A phase 1, open-label study in advanced malignancies. Annals of Oncology 27 (2016) (Supplement 6): vi359-vi378 (Year: 2016).*
Vynnychenko et al. BALTIC: A Phase 2, Open-Label Study of Novel Combinations of Immunotherapies or DDR Inhibitors in Platinum-Refractory ED-SCLC. Journal of Clinical Oncology 2017 35:15_suppl, TPS8585-TPS8585 (Year: 2017).*
Kwok et al. Pembrolizumab (Keytruda). Human Vaccines & Immunotherapeutics (2016) 12(11): 2777-2789 (Year: 2016).*
Paz-Ares et al A phase 3, randomized study of first-line Durvalumab (D) ± tremelimumab (T) + platinum-based chemotherapy (CT) vs CT alone in extensive disease small cell lung cancer (ED-SCLC): Caspian. Journal of Clinical Oncology 2017 35:15_suppl, TPS8586 (Year: 2017).*
Agata et al., "Expression of the PD-1 Antigen on the Surface of Stimulated Mouse T And B Lymphocytes", Int. Immunol., 8(5):765-772, May 1996.
Antonia et al., "Durvalumab after chemoradiotherapy in stage III non-small-cell lung cancer", N Engl J Med, 377:1919-1929, (Nov. 2017), Epub Sep. 2017.
Antonia et al., "Overall survival with durvalumab after chemoradiotherapy in Stage III NSCLC", N Engl J Med, 379:2342-2350, (Dec. 2018), Epub Sep. 2018.
Bondarenko et al., "Preliminary Efficacy of Durvalumab plus Tremelimumab in Platinum-refractory/resistant Extensive Disease—Small Cell Lung Cancer from Cohort A of the Phase 2 BALTIC Study", Ann Oncol, 29(suppl_8):viii596-viii602 (Abstract 1665PD), Oct. 2018.
Burman et al., "A recycling framework for the construction of Bonferroni-based multiple tests", Stat Med, 28:739-61, Jan. 2009.
Byers, et al., "Small cell lung cancer: where do we go from here?", Cancer, 121(5):664-72, (Mar. 2015), Oct. 2014.
Cho et al., "Safety and Clinical Activity of Durvalumab in Combination with Tremelimumab in Extensive Disease Small-Cell Lung Cancer", J Clin Oncol, 36(15_suppl; abstr 8517, Jun. 2018.
Clinical Trial US Gov: , Jan. 1, 2017, XP55749692, Retrieved from the Internet: URL:https//clinicaltrials.gov/ctzshowNCT03043872.
Dibonaventura et al., "Adherence to recommended clinical guidelines in extensive disease small-cell lung cancer across the US, Europe, and Japan", Ther Clin Risk Manag, 15: 355-66, Feb. 2019.
Farago et al., "Current standards for clinical management of small cell lung cancer", Transl Lung Cancer Res 7(1):69-79, Feb. 2018.
Fruh et al., "Small-cell lung cancer (SCLC): ESMO Clinical Practice Guidelines for Diagnosis, Treatment and Follow-up", Ann Oncol, 24(Suppl 6):vi99-105, (Oct. 2013), Epub Jun. 2013.
Fukuoka et al., "Randomized trial of cyclophosphamide, doxorubicin, and vincristine versus cisplatin and etoposide versus alternation of these regimens in small-cell lung cancer", J Natl Cancer Inst, 9; 83(12):855-61, Jun. 1991.
Goldman et al., "Safety and Antitumor Activity of Durvalumab Monotherapy in Patients with Pretreated Extensive Disease Small-Cell Lung Cancer", J Clin Oncol, 36(15_suppl; abstr 8518), Jun. 2018.

(Continued)

*Primary Examiner* — Robert S Landsman
(74) *Attorney, Agent, or Firm* — McDonnell Boehnen Hulbert & Berghoff LLP

(57) ABSTRACT

Disclosed are methods for treating extensive-stage small-cell lung cancer (ES-SCLC) with an antibody that inhibits PD1/PD-L1 activity in combination with etoposide and a platinum-based therapeutic agent.

48 Claims, 11 Drawing Sheets
Specification includes a Sequence Listing.

(56) References Cited

OTHER PUBLICATIONS

Horita et al., "Topotecan for Relapsed Small-cell Lung Cancer: Systematic Review and Meta-Analysis of 1347 Patients", Sci Rep, 5:15437, Oct. 2015.
Horn et al., "First-Line Atezolizumab plus Chemotherapy in Extensive-Stage Small-Cell Lung Cancer", N Engl J Med, 379:2220-9, (Dec. 2018), Epub Sep. 2018.
Ishida, et al., "Induced Expression of PD-1, A Novel Member of the Immunoglobulin Gene Superfamily, Upon Programmed Cell Death", EMBO J. 11: 3887-3895, Nov. 1992.
Lazar-Molnar, et al., "Crystal Structure of the Complex Between Programmed Death-1 (PD-1) and Its Ligand PD-L2", Proc. Natl. Acad. Sci. (USA) 105(30): 10483-10488, Jul. 2008.
Martin-Orozco, et al., "Inhibitory Costimulation and Anti-Tumor Immunity", Semin. Cancer Biol. 17(4):288-298, Aug. 2007.
Nishimura, H. et al., "Facilitation of Beta Selection and Modification of Positive Selection in the Thymus of PD-I-Deficient Mice", J. Exp. Med., 191(5): 891-898, Mar. 2000.
Oronsky, et al., "What's new in SCLC? A review", Neoplasia, 19(10):842-847, (Oct. 2017), Epub Sep. 2017.
Paz-Ares, et al., "Durvalumab plus platinum-etoposide versus platinum-etoposide in first-line treatment of extensive-stage small-cell lung cancer (CASPIAN): a randomised, controlled, open-label, phase 3 trial" Lancet, 394: 1929-39, (Nov. 2019), Epub Oct. 2019.
Pietanza et al., "Small Cell Lung Cancer: Will Recent Progress Lead to Improved Outcomes?", Clin Cancer Res, 21:2244-55, May 2015.
Rossi et al., "Carboplatin- or cisplatin-based chemotherapy in first-line treatment of small-cell lung cancer: the COCIS meta-analysis of individual patient data", J Clin Oncol., 30:1692-98, May 2012.
Rudin et al., "Treatment of small-cell lung cancer: American Society of Clinical Oncology endorsement of the American College of Chest Physicians guideline", J Clin Oncol, 8; 33(34):4106-11, (Dec. 2015), Epub Sep. 2015.
Stewart et al., "Identification and characterization of durvalumab, an antagonistic anti-PD-L1 monoclonal antibody", Cancer Immunol Res, 3(9):1052-62, (Sep. 2015), Epub May 2015.
Subudhi et al., "The Balance of Immune Responses: Costimulation Verse Coinhibition", J. Molec. Med. 83: 193-202, Jan. 2005.
Wang et al., "Survival changes in patients with small cell lung cancer and disparities between different sexes, socioeconomic statuses and ages", Sci Rep, 7:1339, May 2017.
Yamazaki et al., "Expression of Programmed Death 1 Ligands by Murine T Cells and APC", J. Immunol., 169(10):5538-5545, Nov. 2002.
The International Search Report and Written Opinion issued by International Searching Authority for International Application No. PCT/EP2020/074714; dated Nov. 25, 2020 (15 pages).
Fujiwara et al. "Tolerability and efficacy od durvalumab in Japanese patients with advanced solid tumors". Cancer Science, 110(5): 1715-1723, Apr. 2019.
Abbas and Rehman (2018). "An Overview of Cancer Treatment Modalities." In H. N. Shahzad (Ed.), Neoplasm (Chapter 6, pp. 139-157). InTechOpen.
Chabner and Palmer (2019). "Clinical Strategies for Cancer Treatment: The Role of Drugs." In B. Chabner & D. L. Longo (Eds.), Cancer Chemotherapy, Immunotherapy and Biotherapy: Principles and Practice (6th ed., Chapter 1). Wolters Kluwer: Philadelphia, PA.
Devita, et al. (1975). "Combination versus single agent chemotherapy: a review of the basis for selection of drug treatment of cancer." Cancer 35, 98-110.
Wahida, et al. (2023). "The coming decade in precision oncology: six riddles." Nat. Rev. Cancer 23, 43-54.

* cited by examiner

```
                       SEQUENCE LISTING

<160> NUMBER OF SEQ ID NOS: 10

<210> SEQ ID NO 1
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95
```

Trp Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Thr Phe Ser Arg Tyr Trp Met Ser
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Ile Lys Gln Asp Gly Ser Glu Lys Tyr Tyr Val Asp Ser Val Lys
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Glu Gly Gly Trp Phe Gly Glu Leu Ala Phe Asp Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Arg Val Ser Ser Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ala Ser Ser Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Gly Ser Leu Pro Trp Thr
1               5

<210> SEQ ID NO 9
<211> LENGTH: 176
<212> TYPE: PRT
<213> ORGANISM: Homo sapiens

<400> SEQUENCE: 9

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
                20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Asn Glu Ile Phe Tyr Cys Thr
                85                  90                  95

Phe Arg Arg Leu Asp Pro Glu Glu Asn His Thr Ala Glu Leu Val Ile
                100                 105                 110

Pro Glu Leu Pro Leu Ala His Pro Pro Asn Glu Arg Thr His Leu Val
            115                 120                 125

Ile Leu Gly Ala Ile Leu Leu Cys Leu Gly Val Ala Leu Thr Phe Ile
```

| | | | 130 | | | 135 | | | 140 | | |
|---|---|---|---|---|---|---|---|---|---|---|---|
| Phe | Arg | Leu | Arg | Lys | Gly | Arg | Met | Met | Asp | Val | Lys | Lys | Cys | Gly | Ile |
| 145 | | | | 150 | | | | 155 | | | | 160 |

| Gln | Asp | Thr | Asn | Ser | Lys | Lys | Gln | Ser | Asp | Thr | His | Leu | Glu | Glu | Thr |
|---|---|---|---|---|---|---|---|---|---|---|---|---|---|---|---|
| | | | 165 | | | | | 170 | | | | 175 |

<210> SEQ ID NO 10
<211> LENGTH: 3349
<212> TYPE: DNA
<213> ORGANISM: Homo sapiens

<400> SEQUENCE: 10

```
ggcgcaacgc tgagcagctg gcgcgtcccg cgcggcccca gttctgcgca gcttcccgag      60
gctccgcacc agccgcgctt ctgtccgcct gcagggcatt ccagaaagat gaggatattt     120
gctgtcttta tattcatgac ctactggcat ttgctgaacg ccccatacaa caaaatcaac     180
caaagaattt tggttgtgga tccagtcacc tctgaacatg aactgacatg tcaggctgag     240
ggctacccca aggccgaagt catctggaca agcagtgacc atcaagtcct gagtggtaag     300
accaccacca ccaattccaa gagagaggag aagcttttca atgtgaccag cacactgaga     360
atcaacacaa caactaatga dattttctac tgcactttta ggagattaga tcctgaggaa     420
aaccatacag ctgaattggt catcccagaa ctacctctgg cacatcctcc aaatgaaagg     480
actcacttgg taattctggg agccatctta ttatgccttg tgtagcact gacattcatc      540
ttccgtttaa gaaagggag aatgatggat gtgaaaaaat gtggcatcca agatacaaac     600
tcaaagaagc aaagtgatac acatttggag gagacgtaat ccagcattgg aacttctgat     660
cttcaagcag ggattctcaa cctgtggttt aggggttcat cggggctgag cgtgacaaga     720
ggaaggaatg ggcccgtggg atgcaggcaa tgtgggactt aaaaggccca agcactgaaa     780
atggaacctg gcgaaagcag aggaggagaa tgaagaaaga tggagtcaaa cagggagcct     840
ggagggagac cttgatactt tcaaatgcct gaggggctca tcgacgcctg tgacagggag     900
aaaggatact tctgaacaag gagcctccaa gcaaatcatc cattgctcat cctaggaaga     960
cgggttgaga atccctaatt tgagggtcag ttcctgcaga agtgcccttt gcctccactc    1020
aatgcctcaa tttgttttct gcatgactga gagtctcagt gttggaacgg acagtatttt    1080
atgtatgagt ttttcctatt tattttgagt ctgtgaggtc ttcttgtcat gtgagtgtgg    1140
ttgtgaatga tttcttttga agatatattg tagtagatgt tacaattttg tcgccaaact    1200
aaacttgctg cttaatgatt tgctcacatc tagtaaaaca tggagtattt gtaaggtgct    1260
tggtctcctc tataactaca agtatacatt ggaagcataa agatcaaacc gttggttgca    1320
taggatgtca ctttatttta acccattaat actctggttg acctaatctt attctcagac    1380
ctcaagtgtc tgtgcagtat ctgttccatt taaatatcag ctttacaatt atgtggtagc    1440
ctacacacat aatctcattt catcgctgta accaccctgt tgtgataacc actattattt    1500
tacccatcgt acagctgagg aagcaaacag attaagtaac ttgcccaaac cagtaaatag    1560
cagacctcag actgccaccc actgtccttt tataatacaa tttacagcta tattttactt    1620
taagcaattc ttttattcaa aaaccattta ttaagtgccc ttgcaatatc aatcgctgtg    1680
ccaggcattg aatctacaga tgtgagcaag acaaagtacc tgtcctcaag gagctcatag    1740
tataatgagg agattaacaa gaaatgtat tattacaatt tagtccagtg tcatagcata    1800
aggatgatgc gaggggaaaa cccgagcagt gttgccaaga ggaggaaata ggccaatgtg    1860
gtctgggacg gttggatata cttaaacatc ttaataatca gagtaatttt catttacaaa    1920
```

```
gagaggtcgg tacttaaaat aaccctgaaa aataacactg gaattccttt tctagcatta    1980
tatttattcc tgatttgcct ttgccatata atctaatgct tgtttatata gtgtctggta    2040
ttgtttaaca gttctgtctt ttctatttaa atgccactaa attttaaatt cataccttc     2100
catgattcaa aattcaaaag atcccatggg agatggttgg aaaatctcca cttcatcctc    2160
caagccattc aagtttcctt tccagaagca actgctactg cctttcattc atatgttctt    2220
ctaaagatag tctacatttg gaaatgtatg ttaaaagcac gtattttaa aattttttc      2280
ctaaatagta acacattgta tgtctgctgt gtactttgct attttattt attttagtgt     2340
ttcttatata gcagatggaa tgaatttgaa gttcccaggg ctgaggatcc atgccttctt    2400
tgtttctaag ttatctttcc catagctttt cattatcttt catatgatcc agtatatgtt    2460
aaatatgtcc tacatataca tttagacaac caccatttgt taagtatttg ctctaggaca    2520
gagtttggat ttgtttatgt ttgctcaaaa ggagacccat gggctctcca gggtgcactg    2580
agtcaatcta gtcctaaaaa gcaatctat tattaactct gtatgacaga atcatgtctg     2640
gaacttttgt tttctgcttt ctgtcaagta taaacttcac tttgatgctg tacttgcaaa    2700
atcacatttt ctttctggaa attccggcag tgtaccttga ctgctagcta ccctgtgcca    2760
gaaaagcctc attcgttgtg cttgaaccct tgaatgccac cagctgtcat cactacacag    2820
ccctcctaag aggcttcctg gaggtttcga gattcagatg ccctgggaga tcccagagtt    2880
tcctttccct cttggccata ttctggtgtc aatgacaagg agtaccttgg ctttgccaca    2940
tgtcaaggct gaagaaacag tgtctccaac agagctcctt gtgttatctg tttgtacatg    3000
tgcatttgta cagtaattgg tgtgacagtg ttctttgtgt gaattacagg caagaattgt    3060
ggctgagcaa ggcacatagt ctactcagtc tattcctaag tcctaactcc tccttgtggt    3120
gttggatttg taaggcactt tatcccttt gtctcatgtt tcatcgtaaa tggcataggc     3180
agagatgata cctaattctg catttgattg tcacttttg tacctgcatt aatttaataa     3240
aatattctta tttattttgt tacttggtac accagcatgt ccattttctt gtttattttg    3300
tgtttaataa aatgttcagt ttaacatccc agtggagaaa gttaaaaaa                3349
```

METHODS FOR TREATING LATE-STAGE SMALL CELL LUNG CANCER BY ADMINISTERING A HUMAN ANTI-PD-L1 ANTIBODY, AN ETOPOSIDE AND A PLATINUM-BASED THERAPEUTIC

This application claims benefit under 35 U.S.C. § 119(e) of the following U.S. Provisional Application No. 62/896,224 filed Sep. 4, 2019. The above listed application is incorporated by reference herein in its entirety for all purposes.

REFERENCE TO THE SEQUENCE LISTING

This application incorporates by reference a Sequence Listing submitted with this application as text file entitled B7H1-240-US-PCT_SL.txt created on Aug. 14, 2020 and having a size of 10 kilobytes.

FIELD OF THE INVENTION

The present invention generally relates to methods for treating extensive-stage SCLC patients based on use of a combination of durvalumab and platinum-etoposide.

BACKGROUND OF THE INVENTION

Lung cancer is the leading cause of cancer death among both men and women and accounts for about one-fifth of all cancer deaths. Lung cancer is broadly split into non-small-cell lung cancer (NSCLC) and small-cell lung cancer (SCLC), the latter of which accounts for 13-17% of all diagnosed lung cancers and is characterized by rapid proliferation, high growth fraction, and early development of widespread metastases (Oronsky et al. What's new in SCLC? A review. Neoplasia 2017; 19(10):842-847; Wang et al. Survival changes in patients with small cell lung cancer and disparities between different sexes, socioeconomic statuses and ages. Sci Rep 2017; 7:1339). Less than 7% of patients with SCLC remain alive at 5 years following diagnosis (Byers et al. Small cell lung cancer: where do we go from here? Cancer 2015 1; 121(5):664-72; Wang et al., 2017). Extensive-stage SCLC (ES-SCLC), in which the cancer has spread widely through the lung or to other parts of the body, accounts for approximately two-thirds of all cases of SCLC (Oronsky et al., 2017). Prognosis is particularly poor, as only 6% of all SCLC patients will be alive five years after diagnosis.

For more than three decades, the standard of care (first-line treatment) for ES-SCLC has consisted of 4-6 cycles of etoposide plus either cisplatin or carboplatin (EP), with limited alternatives (Pietanza et al. Small Cell Lung Cancer: Will Recent Progress Lead to Improved Outcomes? Clin Cancer Res 2015; 21:2244-55; Frith et al. Small-cell lung cancer (SCLC): ESMO Clinical Practice Guidelines for Diagnosis, Treatment and Follow-up. Ann Oncol 2013; 24(Suppl 6):vi99-105; Rudin et al. Treatment of small-cell lung cancer: American Society of Clinical Oncology endorsement of the American College of Chest Physicians guideline. J Clin Oncol 2015 8; 33(34):4106-11; Japan Lung Cancer Society: Lung cancer practice guidelines 2018 version III. Small cell lung cancer (SCLC)). Despite initial response rates of up to 78% for patients treated with EP (Farago et al. Current standards for clinical management of small cell lung cancer. Transl Lung Cancer Res 2018; 7(1):69-79; Fukuoka et al. Randomized trial of cyclophosphamide, doxorubicin, and vincristine versus cisplatin and etoposide versus alternation of these regimens in small-cell lung cancer. J Natl Cancer Inst 1991; 9; 83(12):855-61), the majority of patients relapse within 6 months of completing initial treatment and median overall survival (OS) is approximately 10 months (Farago et al., 2018; Rossi et al. Carboplatin- or cisplatin-based chemotherapy in first-line treatment of small-cell lung cancer: the COCIS meta-analysis of individual patient data. J Clin Oncol. 2012; 30:1692-98; Pietanza et al., 2015). Outside of Japan, the current standard-of-care treatment in the second-line setting is topotecan (Frith et al., 2013; Rudin et al., 2015), which is associated with poor outcomes (response rates of 5% and a one-year survival rate of 9% in patients with platinum-refractory disease) (Horita et al. Topotecan for Relapsed Small-cell Lung Cancer: Systematic Review and Meta-Analysis of 1347 Patients. Sci Rep 2015; 5:15437), emphasizing the significant unmet need for improved first-line therapies.

Recently, immunotherapy targeting the programmed cell death-1 (PD-1) and programmed cell death ligand-1 (PD-L1) pathway has demonstrated clinical activity for patients with ES-SCLC, including as first-line treatment (Horn et al. First-Line Atezolizumab plus Chemotherapy in Extensive-Stage Small-Cell Lung Cancer. N Engl J Med 2018; 379: 2220-9). Durvalumab, a selective, high-affinity human IgG1 monoclonal antibody that blocks PD-L1 binding to PD-1 and CD80 (Stewart et al. Identification and characterization of durvalumab, an antagonistic anti-PD-L1 monoclonal antibody. Cancer Immunol Res 2015; 3:1052-62), is indicated for the treatment of patients with unresectable, stage III non-small-cell lung cancer following platinum-based chemoradiotherapy (Antonia et al. Durvalumab after chemoradiotherapy in stage III non-small-cell lung cancer. N Engl J Med 2017; 377:1919-1929; Antonia et al. Overall survival with durvalumab after chemoradiotherapy in Stage III NSCLC. N Engl J Med 2018; 379:2342-2350). In early-phase clinical trials, durvalumab, both as monotherapy and in combination with the anti-cytotoxic T lymphocyte-associated antigen-4 (CTLA-4) antibody, tremelimumab, showed durable clinical activity and a manageable safety profile in patients with pretreated ES-SCLC, including those with relapsed or refractory disease (Cho et al. Safety and Clinical Activity of Durvalumab in Combination with Tremelimumab in Extensive Disease Small-Cell Lung Cancer. J Clin Oncol 2018; 36(15_suppl; abstr 8517; Goldman et al. Safety and Antitumor Activity of Durvalumab Monotherapy in Patients with Pretreated Extensive Disease Small-Cell Lung Cancer. J Clin Oncol 2018; 36(15_suppl; abstr 8518); Bondarenko et al. Preliminary Efficacy of Durvalumab plus Tremelimumab in Platinum-refractory/resistant Extensive Disease-Small Cell Lung Cancer from Cohort A of the Phase 2 BALTIC Study. Ann Oncol 2018; 29(suppl_8):viii596-viii602 (Abstract 1665PD)).

To address the significant unmet need for improved first-line therapies, this disclosure provides methods comprising administration of durvalumab, with or without tremelimumab, in combination with EP for the first-line treatment of patients with ES-SCLC. As disclosed herein, the methods provide a significant and unexpected advance to the first-line treatment of patients with ES-SCLC.

SUMMARY OF THE INVENTION

The present disclosure generally relates to methods for treating extensive stage small-cell lung cancer (ES-SCLC) in patients as a first-line therapy, wherein the methods comprises administration of an antibody that inhibits PD1/

PD-L1 activity in combination with etoposide and a platinum-based therapeutic agent, and optionally, an antibody that inhibits CTLA-4.

In a first aspect, the present disclosure provides a method of extending progression-free survival (PFS) in a patient with extensive-stage small cell lung cancer (ES-SCLC), comprising treating the patient with a) a human anti-PD-L1 antibody and b) etoposide and a platinum-based therapeutic agent (EP). In one embodiment of the first aspect, the platinum-based therapeutic agent comprises cisplatin and/or carboplatin. In another embodiment of the first aspect, the human anti-PD-L1 antibody comprises a light chain variable domain comprising the amino acid sequence of SEQ ID NO: 1 and a heavy chain variable domain comprising the amino acid sequence of SEQ ID NO: 2. In one embodiment of the first aspect, the human anti-PD-L1 antibody comprises a VH CDR1 having the amino acid sequence of SEQ ID NO: 3; and a VH CDR2 having the amino acid sequence of SEQ ID NO: 4; and a VH CDR3 having the amino acid sequence of SEQ ID NO: 5; and a VL CDR1 having the amino acid sequence of SEQ ID NO: 6; and a VL CDR2 having the amino acid sequence of SEQ ID NO: 7; and a VL CDR3 having the amino acid sequence of SEQ ID NO: 8. In one embodiment of the first aspect, the human anti-PD-L1 antibody is durvalumab, avelumab, or atezolizumab. In another embodiment of the first aspect, the human anti-PD-L1 antibody is administered as a fixed dose of 1500 mg, intravenously, Q3W. In another embodiment of the first aspect, the human anti-PD-L1 antibody is administered as a dose of 20 mg/kg, intravenously, Q3W. In another embodiment of the first aspect, the method comprises 4 cycles of administration of the human anti-PD-L1 antibody. In embodiment according of the first aspect, the EP is administered as a dose comprising 80-100 mg/m$^2$ etoposide and carboplatin area under the curve 5-6 mg/mL/min or cisplatin 75-80 mg/m$^2$, intravenously, per dose of human anti-PD-L1 antibody.

In one embodiment of the first aspect, the method further comprises administration of 1500 mg human anti-PD-L1 antibody, intravenously, Q4W after completion of 4 cycles of Q3W.

In an embodiment of the first aspect, the method further comprises administration of a human anti-CTLA-4 antibody, intravenously, Q3W. In one embodiment, the human anti-CTLA-4 antibody is tremelimumab. In another embodiment, the tremelimumab is administered as a fixed dose of 75 mg or as a dose of 1 mg/kg.

In another embodiment of the first aspect or other embodiments thereof, the method further comprises administration of prophylactic cranial irradiation to the patient.

In another embodiment of the first aspect or other embodiments thereof, the method further comprises treating the patient with a human anti-PD-1 antibody. In one embodiment, the human anti-PD-1 antibody comprises pembrolizumab (KEYTRUDA®) or nivolumab) (OPDIVO®).

In another embodiment of the first aspect, PFS is increased by at least about five months versus treatment with EP alone.

In a second aspect, the present disclosure provides a method of extending overall survival (OS) in a patient with extensive-stage small cell lung cancer (ES-SCLC), comprising treating the patient with a) a human anti-PD-L1 antibody and b) etoposide and a platinum-based therapeutic agent (EP). In one embodiment of the second aspect, the platinum-based therapeutic agent comprises cisplatin and/or carboplatin. In another embodiment of the second aspect, the human anti-PD-L1 antibody comprises a light chain variable domain comprising the amino acid sequence of SEQ ID NO: 1 and a heavy chain variable domain comprising the amino acid sequence of SEQ ID NO: 2. In one embodiment of the second aspect, the human anti-PD-L1 antibody comprises a VH CDR1 having the amino acid sequence of SEQ ID NO: 3; and a VH CDR2 having the amino acid sequence of SEQ ID NO: 4; and a VH CDR3 having the amino acid sequence of SEQ ID NO: 5; and a VL CDR1 having the amino acid sequence of SEQ ID NO: 6; and a VL CDR2 having the amino acid sequence of SEQ ID NO: 7; and a VL CDR3 having the amino acid sequence of SEQ ID NO: 8. In one embodiment of the second aspect, the human anti-PD-L1 antibody is durvalumab, avelumab, or atezolizumab. In another embodiment of the second aspect, the human anti-PD-L1 antibody is administered as a fixed dose of 1500 mg, intravenously, Q3W. In another embodiment of the second aspect, the human anti-PD-L1 antibody is administered as a dose of 20 mg/kg, intravenously, Q3W. In another embodiment of the second aspect, the method comprises 4 cycles of administration of the human anti-PD-L1 antibody. In embodiment according of the second aspect, the EP is administered as a dose comprising 80-100 mg/m$^2$ etoposide and carboplatin area under the curve 5-6 mg/mL/min or cisplatin 75-80 mg/m$^2$, intravenously, per dose of human anti-PD-L1 antibody.

In one embodiment of the second aspect, the method further comprises administration of 1500 mg human anti-PD-L1 antibody, intravenously, Q4W after completion of 4 cycles of Q3W.

In an embodiment of the second aspect, the method further comprises administration of a human anti-CTLA-4 antibody, intravenously, Q3W. In one embodiment, the human anti-CTLA-4 antibody is tremelimumab. In another embodiment, the tremelimumab is administered as a fixed dose of 75 mg or as a dose of 1 mg/kg.

In another embodiment of the second aspect or other embodiments thereof, the method further comprises administration of prophylactic cranial irradiation to the patient.

In another embodiment of the second aspect or other embodiments thereof, the method further comprises treating the patient with a human anti-PD-1 antibody. In one embodiment, the human anti-PD-1 antibody comprises pembrolizumab (KEYTRUDA®) or nivolumab)(OPDIVO®).

In another embodiment of the second aspect, OS is extended by at least about three months versus treatment with EP alone.

In a third aspect, the present disclosure provides a method of improving overall response rate (ORR) in a patient with extensive-stage small cell lung cancer (ES-SCLC), comprising treating the patient with a) a human anti-PD-L1 antibody and b) etoposide and a platinum-based therapeutic agent (EP). In one embodiment of the third aspect, the platinum-based therapeutic agent comprises cisplatin and/or carboplatin. In another embodiment of the third aspect, the human anti-PD-L1 antibody comprises a light chain variable domain comprising the amino acid sequence of SEQ ID NO: 1 and a heavy chain variable domain comprising the amino acid sequence of SEQ ID NO: 2. In one embodiment of the third aspect, the human anti-PD-L1 antibody comprises a VH CDR1 having the amino acid sequence of SEQ ID NO: 3; and a VH CDR2 having the amino acid sequence of SEQ ID NO: 4; and a VH CDR3 having the amino acid sequence of SEQ ID NO: 5; and a VL CDR1 having the amino acid sequence of SEQ ID NO: 6; and a VL CDR2 having the amino acid sequence of SEQ ID NO: 7; and a VL CDR3 having the amino acid sequence of SEQ ID NO: 8. In one embodiment of the third aspect, the human anti-PD-L1 antibody is durvalumab, avelumab, or atezolizumab. In another embodiment of the third aspect, the human anti-PD-L1 antibody is administered as a fixed dose of 1500 mg, intravenously, Q3W. In another embodiment of the third aspect, the human anti-PD-L1 antibody is administered as a dose of 20 mg/kg, intravenously, Q3W. In another embodiment of the third aspect, the method comprises 4 cycles of administration of the human anti-PD-L1 antibody. In embodiment according of the third aspect, the EP is administered as a dose comprising 80-100 mg/m$^2$ etoposide and carboplatin area under the curve 5-6 mg/mL/min or cisplatin 75-80 mg/m$^2$, intravenously, per dose of human anti-PD-L1 antibody.

In one embodiment of the third aspect, the method further comprises administration of 1500 mg human anti-PD-L1 antibody, intravenously, Q4W after completion of 4 cycles of Q3W.

In an embodiment of the third aspect, the method further comprises administration of a human anti-CTLA-4 antibody, intravenously, Q3W. In one embodiment, the human anti-CTLA-4 antibody is tremelimumab. In another embodiment, the tremelimumab is administered as a fixed dose of 75 mg or as a dose of 1 mg/kg.

In another embodiment of the third aspect or other embodiments thereof, the method further comprises administration of prophylactic cranial irradiation to the patient.

In another embodiment of the third aspect or other embodiments thereof, the method further comprises treating the patient with a human anti-PD-1 antibody. In one embodiment, the human anti-PD-1 antibody comprises pembrolizumab (KEYTRUIDA®) or nivolumab) (OPDIVO®).

In another embodiment of the third aspect, ORR is increased by at least 10% versus treatment with EP alone.

In a fourth aspect, the present disclosure provides a method of treating ES-SCLC in a patient in need thereof, comprising administering to the patient durvalumab and EP, wherein the durvalumab and EP are administered as a first-line treatment, and, optionally, administering to the patient tremelimumab.

In some embodiments of any of the preceding aspects or embodiments thereof, the patient may express genes (i.e., have a phenotype) associated with therapeutic response to a therapy comprising a human anti-PD-1 antibody. In some aspects, the patient is PD-L1 (+). In other aspects, the patient is PD-L1 (−). In some aspects, the patient is EGFR mutation (+). In other aspects, the patient is EGFR mutation (−) or wild type. In some aspects, the patient may express any combination of PD-L1 and EGFR mutation phenotypes.

Other features, aspects, embodiments, and advantages of provided by the disclosure will be apparent from the detailed description that follows.

BRIEF DESCRIPTION OF THE DRAWINGS

FIG. 6A shows overall response rate per RECIST v1.1. FIG. 6B shows duration of response (DoR). OR, odds ratio. D+EP, durvalumab and EP (etoposide and carboplatin or cisplatin).

DETAILED DESCRIPTION

Figure 1:
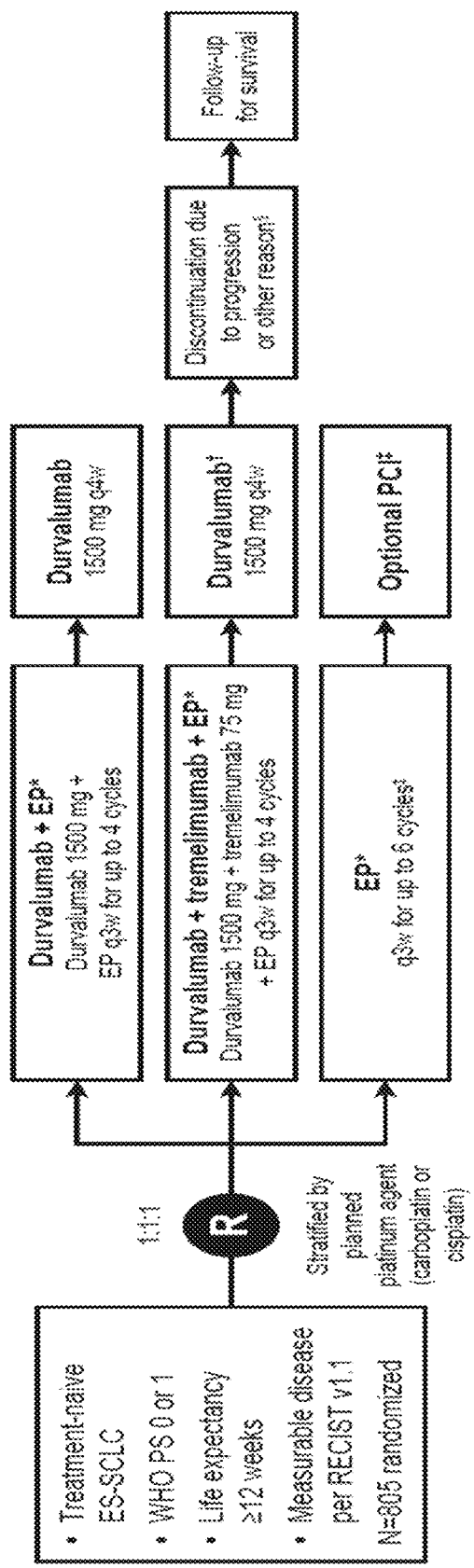
FIG. 1 shows the study design of the present disclosure. *EP consists of etoposide 80-100 mg/m$^2$ with either carboplatin AUC 5-6 or cisplatin 75-80 mg/m$^2$. †Patients received an additional dose of tremelimumab post-EP. ‡Patients could receive an additional 2 cycles of EP (up to 6 cycles total) in the control arm, as well as PCI. § Patients continued treatment until confirmed disease progression, unacceptable toxicity, evidence of a new PNS or worsening of an existing PNS, pregnancy or intent to become pregnant, initiation of alternative anticancer therapy including another investigational agent, noncompliance, or withdrawal of consent. Patients in all arms who had disease progression per RECIST v1.1 (unconfirmed and confirmed) who would continue to receive benefit from their assigned treatment and who met the criteria for treatment in the setting of progressive disease could continue to receive their assigned treatment for as long as they were judged to be gaining clinical benefit. This included EP; however, EP was restricted to a maximum of 4 cycles for patients in the immunotherapy arms and a maximum of 6 cycles for patients in the control arm. AUC, area under the curve; CT, chemotherapy; ES-SCLC, extensive-stage small-cell lung cancer; EP, platinum-etoposide; PCI, prophylactic cranial irradiation; PD; progressive disease; PNS, paraneoplastic syndrome; PS, performance status; q3w, every 3 weeks; q4w, every 4 weeks; RECIST, Response Evaluation Criteria in Solid Tumors; WHO, World Health Organization.

Unless defined otherwise, all technical and scientific terms used herein have the meaning commonly understood by a person skilled in the art to which this invention belongs.

The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing," and "having" and the like can have the meaning ascribed to them in U.S. Patent law and can mean "includes," "including," and the like. The term "consisting essentially of" or "consists essentially" likewise has the meaning ascribed in U.S. Patent law and the term is open-ended, allowing for the presence of more than that which is recited so long as basic or novel characteristics of that which is recited are not changed by the presence of more than that which is recited, but excludes prior art aspects.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an aspect for a variable or aspect herein includes that aspect as any single aspect or in combination with any other aspects or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

By "anti-PD-L1 antibody" is meant an antibody or antigen binding fragment thereof that selectively binds a PD-L1 polypeptide. Exemplary anti-PD-L1 antibodies are described for example at U.S. Pat. Nos. 8,779,108 and 9,493,565, which are herein incorporated by reference. In some aspects durvalumab, avelumab, and atezolizumab is an exemplary PD-L1 antibody. In further aspects, durvalumab is an exemplary PD-L1 antibody.

The term "durvalumab" as used herein refers to an antibody that selectively binds PD-L1 and blocks the binding of PD-L1 to the PD-1 and CD80 receptors, as disclosed in U.S. Pat. No. 9,493,565 (referred to as "2.14H9OPT"), which is incorporated by reference herein in its entirety. The fragment crystallizable (Fc) domain of durvalumab contains a triple mutation in the constant domain of the IgG1 heavy chain that reduces binding to the complement component C1q and the Fcγ receptors responsible for mediating antibody-dependent cell-mediated cytotoxicity (ADCC). Durvalumab can relieve PD-L1-mediated suppression of human T-cell activation in vitro and inhibits tumor growth in a xenograft model via a T-cell dependent mechanism.

By "anti-PD-1 antibody" is meant an antibody or antigen binding fragment thereof that selectively binds a PD-1 polypeptide. In some aspects nivolumab or pembrolizumab is an exemplary PD-1 antibody.

The term "tremelimumab" as used herein refers to an antibody that selectively binds a CTLA-4 polypeptide, as disclosed in U.S. Pat. No. 8,491,895 (referred to as clone 11.2.1), which is incorporated by reference herein in its entirety. Tremelimumab is specific for human CTLA-4, with no cross-reactivity to related human proteins. Tremelimumab blocks the inhibitory effect of CTLA-4, and therefore enhances T-cell activation. Tremelimumab shows minimal specific binding to Fc receptors, does not induce natural killer (NK) antibody-dependent cell-mediated cytotoxicity (ADCC) activity, and does not deliver inhibitory signals following plate-bound aggregation.

A "complete response" (CR) refers to the disappearance of all lesions, whether measurable or not, and no new lesions. Confirmation can be obtained using a repeat, consecutive assessment no less than four weeks from the date of first documentation. New, non-measurable lesions preclude CR.

A "partial response" (PR) refers to a decrease in tumor burden ≥ 50% relative to baseline. Confirmation can be obtained using a consecutive repeat assessment at least 4 weeks from the date of first documentation.

"Progressive disease" (PD) refers to an increase in tumor burden ≥ 25% relative to the minimum recorded (nadir). Confirmation can be obtained by a consecutive repeat assessment at least 4 weeks from the date of first documentation. New, non-measurable lesions do not define PD.

"Stable disease" (SD) refers to not meeting the criteria for CR, PR, or PD. SD indicates a decrease in tumor burden of 50% relative to baseline cannot be established and a 25% increase compared to nadir cannot be established.

As referred to herein, "PD-L1" may refer to polypeptide or polynucleotide sequences, or fragments thereof, having at least about 85%, 95% or 100% sequence identity to PD-L1 sequences. PD-L1 is also referred to in the art as B7-H1. In some aspects, the PD-L1 polypeptide, or fragment thereof, has at least about 85%, 95% or 100% sequence identity to NCBI Accession No. NP_001254635, and has PD-1 and CD80 binding activity.

```
PD-L1 polypeptidesequence (NCBI Accession
No. NP_001254635; SEQ ID NO: 9):
    1 MRIFAVFIFM TYWHLLNAPY NKINQRILVV DPVTSEHELT
      CQAEGYPKAE VIWTSSDHQV

61 LSGKTTTTNS KREEKLFNVT STLRINTTTN EIFYCTFRRL
      DPEENHTAEL VIPELPLAHP

121 PNERTHLVIL GAILLCLGVA LTFIFRLRKG RMMDVKKCGI
      QDTNSKKQSD THLEET
```

In some aspects, a "PD-L1 nucleic acid molecule" comprises a polynucleotide encoding a PD-L1 polypeptide. An exemplary PD-L1 nucleic acid molecule sequence is provided at NCBI Accession No. NM_001267706.

```
PD-L1 nucleic acid sequence (NCBI Accession
No. NM_001267706 mRNA; SEQ ID NO: 10):
    1 ggcgcaacgc tgagcagctg gcgcgtcccg cgcggcccca
      gttctgcgca gcttcccgag 61 gctccgcacc agccgcgctt ctgtccgcct gcagggcatt
      ccagaaagat gaggatattt 121 gctgtcttta tattcatgac ctactggcat ttgctgaacg
      ccccatacaa caaaatcaac
```

```
 181 caaagaattt tggttgtgga tccagtcacc tctgaacatg
     aactgacatg tcaggctgag 241 ggctacccca aggccgaagt catctggaca agcagtgacc
     atcaagtcct gagtggtaag 301 accaccacca ccaattccaa gagagaggag aagcttttca
     atgtgaccag cacactgaga 361 atcaacacaa caactaatga gattttctac tgcactttta
     ggagattaga tcctgaggaa 421 aaccatacag ctgaattggt catcccagaa ctacctctgg
     cacatcctcc aaatgaaagg 481 actcacttgg taattctggg agccatctta ttatgccttg
     gtgtagcact gacattcatc 541 ttccgtttaa gaaaaggag aatgatggat gtgaaaaaat
     gtggcatcca agatacaaac 601 tcaaagaagc aaagtgatac acatttggag gagacgtaat
     ccagcattgg aacttctgat 661 cttcaagcag ggattctcaa cctgtggttt aggggttcat
     cggggctgag cgtgacaaga 721 ggaaggaatg ggcccgtggg atgcaggcaa tgtgggactt
     aaaaggccca agcactgaaa 781 atggaacctg gcgaaagcag aggaggagaa tgaagaaaga
     tggagtcaaa cagggagcct 841 ggagggagac cttgatactt tcaaatgcct gagggctca
     tcgacgcctg tgacagggag 901 aaaggatact tctgaacaag gagcctccaa gcaaatcatc
     cattgctcat cctaggaaga 961 cgggttgaga atccctaatt tgagggtcag ttcctgcaga
     agtgcccttt gcctccactc 1021 aatgcctcaa tttgttttct gcatgactga gagtctcagt
     gttggaacgg gacagtattt 1081 atgtatgagt ttttcctatt tattttgagt ctgtgaggtc
     ttcttgtcat gtgagtgtgg 1141 ttgtgaatga tttcttttga agatatattg tagtagatgt
     tacaattttg tcgccaaact 1201 aaacttgctg cttaatgatt tgctcacatc tagtaaaaca
     tggagtattt gtaaggtgct 1261 tggtctcctc tataactaca agtatacatt ggaagcataa
     agatcaaacc gttggttgca 1321 taggatgtca cctttatta acccattaat actctggttg
     acctaatctt attctcagac 1381 ctcaagtgtc tgtgcagtat ctgttccatt taaatatcag
     ctttacaatt atgtggtagc 1441 ctacacacat aatctcattt catcgctgta accaccctgt
     tgtgataacc actattattt 1501 tacccatcgt acagctgagg aagcaaacag attaagtaac
     ttgcccaaac cagtaaatag 1561 cagacctcag actgccaccc actgtccttt tataatacaa
     tttacagcta tattttactt 1621 taagcaattc ttttattcaa aaaccattta ttaagtgccc
     ttgcaaatatc aatcgctgtg 1681 ccaggcattg aatctacaga tgtgagcaag acaaagtacc
     tgtcctcaag gagctcatag 1741 tataatgagg agattaacaa gaaatgtat tattacaatt
     tagtccagtg tcatagcata 1801 aggatgatgc gaggggaaaa cccgagcagt gttgccaaga
     ggaggaaata ggccaatgtg 1861 gtctgggacg gttggatata cttaaacatc ttaataatca
     gagtaatttt catttacaaa 1921 gagaggtcgg tacttaaaat aaccctgaaa ataacactg
     gaattccttt tctagcatta 1981 tatttattcc tgatttgcct ttgccatata atctaatgct
     tgtttatata gtgtctggta 2041 ttgtttaaca gttctgtctt ttctatttaa atgccactaa
     attttaaatt cataccttc 2101 catgattcaa aattcaaaag atcccatggg agatggttgg
     aaaatctcca cttcatcctc 2161 caagccattc aagtttcctt tccagaagca actgctactg
     cctttcattc atatgttctt 2221 ctaaagatag tctacatttg gaaatgtatg ttaaaagcac
     gtattttaa aatttttttc 2281 ctaaatagta acacattgta tgtctgctgt gtactttgct
     attttatt attttagtgt 2341 ttcttatata gcagatggaa tgaatttgaa gttcccaggg
     ctgaggatcc atgccttctt 2401 tgtttctaag ttatcttttcc catagctttt cattatcttt
     catatgatcc agtatatgtt 2461 aaatatgtcc tacatataca tttagacaac caccatttgt
     taagtatttg ctctaggaca 2521 gagtttggat ttgtttatgt ttgctcaaaa ggagacccat
     gggctctcca gggtgcactg 2581 agtcaatcta gtcctaaaaa gcaatcttat tattaactct
     gtatgacaga atcatgtctg 2641 gaactttgt tttctgcttt ctgtcaagta taaacttcac
     tttgatgctg tacttgcaaa 2701 atcacatttt ctttctggaa attccggcag tgtaccttga
     ctgctagcta ccctgtgcca 2761 gaaaagcctc attcgttgtg cttgaaccct tgaatgccac
     cagctgtcat cactacacag 2821 ccctcctaag aggcttcctg gaggtttcga gattcagatg
     ccctgggaga tcccagagtt 2881 tccttccct cttggccata ttctggtgtc aatgacaagg
     agtaccttgg ctttgccaca 2941 tgtcaaggct gaagaaacag tgtctccaac agagctcctt
     gtgttatctg tttgtacatg 3001 tgcatttgta cagtaattgg tgtgacagtg ttctttgtgt
     gaattacagg caagaattgt 3061 ggctgagcaa ggcacatagt ctactcagtc tattcctaag
     tcctaactcc tccttgtggt 3121 gttggatttg taaggcactt tatccctttt gtctcatgtt
     tcatcgtaaa tggcataggc 3181 agagatgata cctaattctg catttgattg tcactttttg
     tacctgcatt aatttaataa 3241 aatattctta tttattttgt tacttggtac accagcatgt
     ccatttcctt gtttattttg 3301 tgtttaataa aatgttcagt ttaacatccc agtggagaaa
     gttaaaaaa
```

Programmed Death-1 ("PD-1") is an approximately 31 kD type I membrane protein member of the extended CD28/CTLA4 family of T cell regulators (see, Ishida, Y. et al. (1992) Induced Expression Of PD-1, A Novel Member Of The Immunoglobulin Gene Superfamily, Upon Programmed Cell Death," EMBO J. 11:3887-3895). PD-1 is expressed on activated T cells, B cells, and monocytes (Agata et al. (1996) "Expression Of The PD-1 Antigen On The Surface Of Stimulated Mouse T And B Lymphocytes," Int. Immunol. 8(5):765-772; Yamazaki et al. (2002) "Expression Of Programmed Death 1 Ligands By Murine T Cells And APC," J. Immunol. 169:5538-5545) and at low levels in natural killer (NK) T cells (Nishimura, H. et al. (2000) "Facilitation of Beta Selection and Modification of Positive Selection in the Thymus of PD-1-Deficient Mice," J. Exp. Med. 191: 891-898; Martin-Orozco et al. (2007) "Inhibitory Costimulation And Anti-Tumor Immunity," Semin. Cancer Biol. 17(4):288-298). PD-1 is a receptor responsible for down-regulation of the immune system following activation by binding of PD-L1 or PD-L2 (Martin-Orozco, N. et al. (2007) "Inhibitory Costimulation and Anti-Tumor Immunity," Semin. Cancer Biol. 17(4):288-298) and functions as a cell death inducer (Ishida, Y. et al. (1992) "Induced Expression of PD-1, A Novel Member of the Immunoglobulin Gene Superfamily, Upon Programmed Cell Death," EMBO J. 11: 3887-3895; Subudhi, S. K. et al. (2005) "The Balance Of Immune Responses: Costimulation Verse Coinhibition," J. Molec. Med. 83: 193-202) (Lazar-Molnar, E. et al. (2008) "Crystal Structure of the Complex Between Programmed Death-1 (PD-1) And Its Ligand PD-L2," Proc. Natl. Acad. Sci. (USA) 105(30): 10483-10488). This process is exploited in many tumors via the over-expression of PD-L1, leading to a suppressed immune response.

PD-1 is a well-validated target for immune mediated therapy in oncology, with positive clinical trials in the treatment of melanoma and non-small cell lung cancers (NSCLC), among others. Antagonistic inhibition of the PD-1/PD-L1 interaction increases T cell activation, enhancing recognition and elimination of tumor cells by the host immune system. The use of anti-PD-1 antibodies to treat infections and tumors and up-modulate an adaptive immune response has been proposed.

The term "antibody," as used in this disclosure, refers to an immunoglobulin or a fragment or a derivative thereof, and encompasses any polypeptide comprising an antigen-binding site, regardless whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')2, Fv, scFv, Fd, dAb, and other antibody fragments that retain antigen-binding function, e.g., the ability to bind PD-L1 specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region (VL) and an antibody heavy chain variable region (VH); however, it does not necessarily have to comprise both. For example, a so-called Fd antibody fragment consists only of a VH domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in an F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CH1 domain of the heavy chain.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences.

By "specifically binds" is meant a compound (e.g., antibody) that recognizes and binds a molecule (e.g., polypeptide), but which does not substantially recognize and bind other molecules in a sample, for example, a biological sample. For example, two molecules that specifically bind form a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or more preferably higher than $10^8$ $M^{-1}$. If necessary, non-specific binding can be reduced without substantially affecting specific binding by varying the binding conditions. The appropriate binding conditions such as concentration of antibodies, ionic strength of the solution, temperature, time allowed for binding, concentration of a blocking agent (e.g., serum albumin, milk casein), etc., may be optimized by a skilled artisan using routine techniques.

As generally used herein, the terms "treat," treating," "treatment," and the like refer to reducing, ameliorating, or slowing the progression of a disorder or disease and/or symptoms associated with a disorder or disease. It will be appreciated that, although not precluded, treating a disorder, disease, or condition does not require that the disorder, disease, or condition or associated symptoms be completely eliminated. In particular aspects and aspects relating to NSCLC, "treat," treating," "treatment," can refer to achieving any one or combination of primary or secondary clinical endpoints.

Sequences

Durvalumab light chain variable region amino acid sequence is provided as SEQ ID NO: 1.

Durvalumab heavy chain variable region amino acid sequence is provided as SEQ ID NO: 2.

Durvalumab heavy chain variable region amino acid sequence of CDR1, CDR2, and CDR3 are provided as SEQ ID NO: 3 (CDR1), SEQ ID NO: 4 (CDR2), and SEQ ID NO: 5 (CDR3).

Durvalumab light chain variable region amino acid sequence of CDR1, CDR2, and CDR3 are provided as SEQ ID NO: 6 (CDR1), SEQ ID NO: 7 (CDR2), and SEQ ID NO: 8 (CDR3).

The disclosure relates to methods of treating patients who have extensive-stage small cell lung cancer (ES-SCLC), comprising administering to the patient a human anti-PD-L1 antibody in combination with etoposide and a platinum-based therapeutic agent. Further, the method can also include administration of a human anti-CTLA-4 antibody. In particular, the data derived from the clinical results disclosed herein provide for improved treatment methods and substantially redefine the existing standard of care (first-line treatment) for ES-SCLC. The disclosed methods of treatment can provide for substantial improvement in a patient's overall survival (OS), progression-free survival (PFS), overall response rate (ORR), duration of response (DoR), or time to death.

Thus, in the various aspects described herein, the disclosed methods provide new, first-line treatment options for treating a patient with ES-SCLC.

In a first aspect, the present disclosure provides a method of extending progression-free survival (PFS) in a patient with extensive-stage small cell lung cancer (ES-SCLC), comprising treating the patient with a) a human anti-PD-L1 antibody and b) etoposide and a platinum-based therapeutic agent (EP). In one embodiment of the first aspect, the platinum-based therapeutic agent comprises cisplatin and/or carboplatin. In another embodiment of the first aspect, the human anti-PD-L1 antibody comprises a light chain variable domain comprising the amino acid sequence of SEQ ID NO: 1 and a heavy chain variable domain comprising the amino acid sequence of SEQ ID NO: 2. In one embodiment of the first aspect, the human anti-PD-L1 antibody comprises a VH CDR1 having the amino acid sequence of SEQ ID NO: 3; and a VH CDR2 having the amino acid sequence of SEQ ID NO: 4; and a VH CDR3 having the amino acid sequence of SEQ ID NO: 5; and a VL CDR1 having the amino acid sequence of SEQ ID NO: 6; and a VL CDR2 having the amino acid sequence of SEQ ID NO: 7; and a VL CDR3 having the amino acid sequence of SEQ ID NO: 8. In one embodiment of the first aspect, the human anti-PD-L1 antibody is durvalumab, avelumab, or atezolizumab. In another embodiment of the first aspect, the human anti-PD-L1 antibody is administered as a fixed dose of 1500 mg, intravenously, Q3W. In another embodiment of the first aspect, the human anti-PD-L1 antibody is administered as a dose of 20 mg/kg, intravenously, Q3W. In another embodiment of the first aspect, the method comprises 4 cycles of administration of the human anti-PD-L1 antibody. In embodiment according of the first aspect, the EP is administered as a dose comprising 80-100 mg/m$^2$ etoposide and carboplatin area under the curve 5-6 mg/mL/min or cisplatin 75-80 mg/m$^2$, intravenously, per dose of human anti-PD-L1 antibody.

In one embodiment of the first aspect, the method further comprises administration of 1500 mg human anti-PD-L1 antibody, intravenously, Q4W after completion of 4 cycles of Q3W.

In an embodiment of the first aspect, the method further comprises administration of a human anti-CTLA-4 antibody, intravenously, Q3W. In one embodiment, the human anti-CTLA-4 antibody is tremelimumab. In another embodiment, the tremelimumab is administered as a fixed dose of 75 mg or as a dose of 1 mg/kg.

In another embodiment of the first aspect or other embodiments thereof, the method further comprises administration of prophylactic cranial irradiation to the patient.

In another embodiment of the first aspect or other embodiments thereof, the method further comprises treating the patient with a human anti-PD-1 antibody. In one embodiment, the human anti-PD-1 antibody comprises pembrolizumab (KEYTRUIDA®) or nivolumab) (OPDIVO®).

In another embodiment of the first aspect, PFS is increased by at least about five months versus treatment with EP alone.

In a second aspect, the present disclosure provides a method of extending overall survival (OS) in a patient with extensive-stage small cell lung cancer (ES-SCLC), comprising treating the patient with a) a human anti-PD-L1 antibody and b) etoposide and a platinum-based therapeutic agent (EP). In one embodiment of the second aspect, the platinum-based therapeutic agent comprises cisplatin and/or carboplatin. In another embodiment of the second aspect, the human anti-PD-L1 antibody comprises a light chain variable domain comprising the amino acid sequence of SEQ ID NO: 1 and a heavy chain variable domain comprising the amino acid sequence of SEQ ID NO: 2. In one embodiment of the second aspect, the human anti-PD-L1 antibody comprises a VH CDR1 having the amino acid sequence of SEQ ID NO: 3; and a VH CDR2 having the amino acid sequence of SEQ ID NO: 4; and a VH CDR3 having the amino acid sequence of SEQ ID NO: 5; and a VL CDR1 having the amino acid sequence of SEQ ID NO: 6; and a VL CDR2 having the amino acid sequence of SEQ ID NO: 7; and a VL CDR3 having the amino acid sequence of SEQ ID NO: 8. In one embodiment of the second aspect, the human anti-PD-L1 antibody is durvalumab, avelumab, or atezolizumab. In another embodiment of the second aspect, the human anti-PD-L1 antibody is administered as a fixed dose of 1500 mg, intravenously, Q3W. In another embodiment of the second aspect, the human anti-PD-L1 antibody is administered as a dose of 20 mg/kg, intravenously, Q3W. In another embodiment of the second aspect, the method comprises 4 cycles of administration of the human anti-PD-L1 antibody. In embodiment according of the second aspect, the EP is administered as a dose comprising 80-100 mg/m$^2$ etoposide and carboplatin area under the curve 5-6 mg/mL/min or cisplatin 75-80 mg/m$^2$, intravenously, per dose of human anti-PD-L1 antibody.

In one embodiment of the second aspect, the method further comprises administration of 1500 mg human anti-PD-L1 antibody, intravenously, Q4W after completion of 4 cycles of Q3W.

In an embodiment of the second aspect, the method further comprises administration of a human anti-CTLA-4 antibody, intravenously, Q3W. In one embodiment, the human anti-CTLA-4 antibody is tremelimumab. In another embodiment, the tremelimumab is administered as a fixed dose of 75 mg or as a dose of 1 mg/kg.

In another embodiment of the second aspect or other embodiments thereof, the method further comprises administration of prophylactic cranial irradiation to the patient.

In another embodiment of the second aspect or other embodiments thereof, the method further comprises treating the patient with a human anti-PD-1 antibody. In one embodiment, the human anti-PD-1 antibody comprises pembrolizumab (KEYTRUDA®) or nivolumab)(OPDIVO®).

In another embodiment of the second aspect, OS is extended by at least about three months versus treatment with EP alone.

In a third aspect, the present disclosure provides a method of improving overall response rate (ORR) in a patient with extensive-stage small cell lung cancer (ES-SCLC), comprising treating the patient with a) a human anti-PD-L1 antibody and b) etoposide and a platinum-based therapeutic agent (EP). In one embodiment of the third aspect, the platinum-based therapeutic agent comprises cisplatin and/or carboplatin. In another embodiment of the third aspect, the human anti-PD-L1 antibody comprises a light chain variable domain comprising the amino acid sequence of SEQ ID NO: 1 and a heavy chain variable domain comprising the amino acid sequence of SEQ ID NO: 2. In one embodiment of the third aspect, the human anti-PD-L1 antibody comprises a VH CDR1 having the amino acid sequence of SEQ ID NO: 3; and a VH CDR2 having the amino acid sequence of SEQ ID NO: 4; and a VH CDR3 having the amino acid sequence of SEQ ID NO: 5; and a VL CDR1 having the amino acid sequence of SEQ ID NO: 6; and a VL CDR2 having the amino acid sequence of SEQ ID NO: 7; and a VL CDR3 having the amino acid sequence of SEQ ID NO: 8. In one embodiment of the third aspect, the human anti-PD-L1 antibody is durvalumab, avelumab, or atezolizumab. In another embodiment of the third aspect, the human anti-PD-L1 antibody is administered as a fixed dose of 1500 mg, intravenously, Q3W. In another embodiment of the third aspect, the human anti-PD-L1 antibody is administered as a dose of 20 mg/kg, intravenously, Q3W. In another embodiment of the third aspect, the method comprises 4 cycles of administration of the human anti-PD-L1 antibody. In embodiment according of the third aspect, the EP is administered as a dose comprising 80-100 mg/m$^2$ etoposide and carboplatin area under the curve 5-6 mg/mL/min or cisplatin 75-80 mg/m$^2$, intravenously, per dose of human anti-PD-L1 antibody.

In one embodiment of the third aspect, the method further comprises administration of 1500 mg human anti-PD-L1 antibody, intravenously, Q4W after completion of 4 cycles of Q3W.

In an embodiment of the third aspect, the method further comprises administration of a human anti-CTLA-4 antibody, intravenously, Q3W. In one embodiment, the human anti-CTLA-4 antibody is tremelimumab. In another embodiment, the tremelimumab is administered as a fixed dose of 75 mg or as a dose of 1 mg/kg.

In another embodiment of the third aspect or other embodiments thereof, the method further comprises administration of prophylactic cranial irradiation to the patient.

In another embodiment of the third aspect or other embodiments thereof, the method further comprises treating the patient with a human anti-PD-1 antibody. In one embodiment, the human anti-PD-1 antibody comprises pembrolizumab (KEYTRUDA®) or nivolumab) (OPDIVO®).

In another embodiment of the third aspect, ORR is increased by at least 10% versus treatment with EP alone.

In a fourth aspect, the present disclosure provides a method of treating ES-SCLC in a patient in need thereof, comprising administering to the patient durvalumab and EP, wherein the durvalumab and EP are administered as a first-line treatment, and, optionally, administering to the patient tremelimumab.

In some embodiments of any of the preceding aspects or embodiments thereof, the patient may express genes (i.e., have a phenotype) associated with therapeutic response to a therapy comprising a human anti-PD-1 antibody. In some aspects, the patient is PD-L1 (+). In other aspects, the patient is PD-L1 (−). In some aspects, the patient is EGFR mutation (+). In other aspects, the patient is EGFR mutation (−) or wild type. In some aspects, the patient may express any combination of PD-L1 and EGFR mutation phenotypes.

In addition to the above aspects, the treatments disclosed herein can comprise administering an anti-PD-L1 antibody or an antigen-binding fragment thereof intravenously once every 2, 3, or 4 weeks, at a dosage of 10 mg/kg or 20 mg/kg.

In addition to the above aspects, the treatments disclosed herein can comprise administering of an anti-PD-L1 antibody or an antigen-binding fragment thereof intravenously once every 2, 3, or 4 weeks at a fixed dose of 200, 250, 500, 1000, or 1500 mg.

In aspects of the above aspects, the patient may express genes (i.e., have a phenotype) associated with therapeutic response to a therapy comprising a human anti-PD-L1 antibody. In some aspects, the patient is PD-L1 (+). In other aspects, the patient is PD-L1 (−). A sample was determined to be "PD-L1 positive" if the sample contained 25% or more tumor cells with PD-L1 membrane staining. A cutoff and scoring algorithm has been previously determined for durvalumab (Study CP1108; ClinicalTrials.gov number NCT01693562).

In some aspects, the patient is EGFR mutation (+). In other aspects, the patient is EGFR mutation (−) or wild type. In some aspects, the patient may express any combination of PD-L1 and EGFR mutation phenotypes.

In addition to the above aspects, the treatments disclosed herein can comprise administering a given dose of therapeutic agents (antibodies and/or chemotherapeutic agents) about every 14 days, or every 3 weeks, or every 4 weeks, for up to 52 weeks or longer.

Overall Survival (OS) relates to the time period beginning on the date of treatment until death due to any cause. OS may refer to overall survival within a period of time such as, for example, 12 months, 18 months, 24 months, and the like. Such periods of time can be identified, for example, as "OS24" which refers to the number (%) of patients who are alive at 24 months after treatment onset per the Kaplan-Meier estimate of overall survival at 24 months.

Progression-Free Survival (PFS) relates to the time period beginning on the date of treatment until the date of objective disease progression (RECIST 1.1) or death (by any cause in the absence of progression). In some aspects the methods provide for increase in PFS. In some aspects the methods provide for PFS of at least 9 months to at least about 24 months (e.g., at least 9, 10, 11, 12, 13, 14, 15, 16, 17, 18, 19, 20, 21, 22, 23, 24, or more months, and up to about 5 years).

Duration of Response (DoR) refers to the time from the date for first documented response of Complete Response (CR) or Partial Response (PR) until the first documented response of progression per RECIST 1.1 or death in the absence of progression. In aspects the methods provide for an increase in DoR of at least about 9 months to at least about 36 months.

Objective Response Rate (ORR) refers to the number (%) of patients with at least one visit response of Complete Response (CR) or partial response (PR) per RECIST 1.1. In aspects the methods provide for an increase in DoR of at least about 9 months to at least about 36 months.

The disclosed methods comprise administration of an immunotherapeutic agent (e.g., a human anti-PD-L1 antibody or a human anti-PD-1 antibody) in combination with a chemotherapeutic agent (e.g., etoposide and a platinum-based therapeutic agent, such as, for example, cisplatin and/or carboplatin).

As mentioned above, and as illustrated herein, the methods treat patients with ES-SCLC.

Cancer staging can be performed using any tests that are generally known and accepted in the art. In certain aspects, cancer staging can comprise the American Joint Committee on Cancer's (AJCC's) TNM system. Generally the TNM system provides results from various tests and scans in order to determine the size and location of the primary tumor (Tumor, T); whether the cancer has spread to the lymph nodes, and if it has, the location and number of the affected lymph nodes (Node, N); and whether the cancer has spread to other parts of the body, and if it has, the extent and location of the remote cancer (Metastasis, M). While each type of cancer may have its own specific system, the TNM staging system generally uses scaled scoring for each letter.

For Tumor, "T" is associated with a number (e.g., 0 to 4) to describe the general tumor size, location, and whether it intrudes into nearby tissues. Larger or more intrusive tumors are given a higher number and, depending on the cancer, a lowercase letter, such as "a," "b," or "m" (for multiple), may be added to provide more detail.

Similarly for Node, "N" is associated with a number (e.g., 0 to 3) to describe whether cancer has been found in the lymph nodes, and can also indicate the number of lymph nodes containing cancer. Larger numbers are assigned when more lymph nodes are involved with cancer.

For Metastasis, "M" indicates whether or not the cancer has spread to other parts of the body and is labeled M0 for no spread, or M1 as spread.

The T, N, and M results are combined to determine the stage of cancer, typically one of four stages: stages I (one) to IV (four). Some cancers also have a stage 0 (zero). Stage 0 describes cancer in situ, remaining local to the original tissue without any spread to nearby tissues. This stage of cancer is often highly curable, usually by removing the entire tumor with surgery. Stage I or early-stage cancer, is typically used to describe a small cancer or tumor that has not grown deeply into nearby tissues, and has not spread to the lymph nodes or other parts of the body. Stage II and III describe larger cancers or tumors that have grown more deeply into nearby tissue, and that may have also spread to lymph nodes but not metastasized to other tissues. Stage IV describes a cancer that has spread to other organs or parts of the body and often identified as advanced or metastatic cancer.

Staging may include optional analysis of prognostic factors to provide chances of recovery and a recommended therapy. Prognostic factors may include grading the cancer based on appearance of the cancer cells; analysis of tumor marker expression; and analysis of tumor genetics.

The TNM system can be used for both SCLC and NSCLC, but SCLC is typically staged using a different system.

Staging of SCLC

SCLC has 2 stages: "limited-stage" and "extensive-stage." Limited-stage SCLC indicates that the cancer is only on one side of the chest and can be treated with a single radiation field. Typically, limited-stage SCLC includes cancers that are in only one lung, and that might have reached lymph nodes on the same side of the chest. An exception would be SCLC with tumors that are spread throughout a single lung such that the cancer is not confined to an area small enough to be treated with radiation therapy in one "port." Such cancers are considered to be extensive-stage even though they are only on one side.

The second stage of SCLC or "extensive-stage" SCLC are those SCLC cancers with tumor spread beyond a radiation therapy treatment area of one port, such as cancers that have spread widely throughout a single lung, to the opposite lung, to lymph nodes on the other side of the chest, to other parts of the body, or to the fluid around the lung.

Anti-PD-L1 Antibodies

Antibodies that specifically bind and inhibit PD-L1 activity (e.g., binding to PD-1 and/or CD80) are useful in the methods disclosed herein.

Durvalumab is an exemplary anti-PD-L1 antibody that is selective for PD-L1 and blocks the binding of PD-L1 to the PD-1 and CD80 receptors. Durvalumab can relieve PD-L1-mediated suppression of human T-cell activation in vitro and inhibits tumor growth in a xenograft model via a T-cell dependent mechanism. Other agents that are useful in the disclosed methods include agents that inhibit PD-L1 and/or PD-1, such as, for example the human anti-PD-L1 antibodies avelumab and atezolizumab, or the human anti-PD-1 antibodies nivolumab and pembrolizumab.

In certain aspects, an antibody that is used in the methods disclosed herein is any agent that disrupts the PD-1/PD-L1 axis.

Information regarding Durvalumab (or fragments thereof) for use in the methods provided herein can be found in U.S. Pat. Nos. 8,779,108 and 9,493,565, the disclosures of which are incorporated herein by reference in its entirety. The fragment crystallizable (Fc) domain of durvalumab contains a triple mutation in the constant domain of the IgG1 heavy chain that reduces binding to the complement component C1q and the Fcγ receptors responsible for mediating antibody-dependent cell-mediated cytotoxicity (ADCC).

Durvalumab and antigen-binding fragments thereof for use in the methods provided herein comprises a heavy chain and a light chain or a heavy chain variable region and a light chain variable region. In a specific aspect, durvalumab or an antigen-binding fragment thereof for use in the methods provided herein comprises a light chain variable region comprising the amino acid sequence of SEQ ID NO: 1 and a heavy chain variable region comprising the amino acid sequence of SEQ ID NO: 2. In a specific aspect, durvalumab or an antigen-binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs: 3-5, and wherein the light chain variable region comprises the Kabat-defined CDR1, CDR2, and CDR3 sequences of SEQ ID NOs: 6-8. Those of ordinary skill in the art would easily be able to identify Chothia-defined, Abm-defined or other CDR definitions known to those of ordinary skill in the art. In a specific aspect, durvalumab or an antigen-binding fragment thereof for use in the methods provided herein comprises the variable heavy chain and variable light chain CDR sequences of the 2.14H9OPT antibody as disclosed in U.S. Pat. Nos. 8,779,108 and 9,493,565, which are herein incorporated by reference in their entirety.

As disclosed herein, patients with ES-SCLC can be administered therapeutic agents such as, an anti-PD-1 antibody, and/or an antigen-binding fragment thereof, and/or an anti-PD-L1 antibody, such as durvalumab, and/or an antigen-binding fragment thereof, along with EP, and optionally an anti-CTLA-4 antibody, and/or an antigen-binding fragment thereof, to treat ES-SCLC. Some or all of these therapeutic agents can be administered once in a cycle that lasts two, three, four, or six weeks (or shorter or longer) and each cycle repeated for as long as the treatment provides benefit to the patient. In further aspects, the patient can be administered additional follow-on doses after completion of one or more cycles containing some or all of these therapeutic agents with a subset of therapeutic agents (e.g., only a single therapeutic agent). Follow-on doses can be administered at various time intervals depending on the patient's age, weight, clinical assessment, tumor burden, and/or other factors, including the judgment of the attending physician.

In certain aspects, the interval between doses can be every three weeks. In certain aspects, the interval between doses can be every four weeks. In further aspects, the intervals between doses can be every two months (e.g., during a follow on dosing period and/or maintenance phase).

The amount of durvalumab or an antigen-binding fragment thereof to be administered to the patient may be adjusted and can depend on various parameters, such as the patient's age, weight, clinical assessment, tumor burden and/or other factors, including the judgment of the attending physician. In some aspects, the dose is a fixed dose.

In certain aspects the patient is administered one or more doses of durvalumab wherein the dose is about 1 mg/kg. In certain aspects the patient is administered one or more doses of durvalumab wherein the dose is about 3 mg/kg. In certain aspects the patient is administered one or more doses of durvalumab wherein the dose is about 10 mg/kg. In certain aspects the patient is administered one or more doses of durvalumab wherein the dose is about 15 mg/kg. In certain aspects the patient is administered one or more doses of durvalumab wherein the dose is about 20 mg/kg.

In certain aspects the patient is administered one or more doses of durvalumab wherein the dose is a fixed dose of 1500 mg.

In certain aspects, the patient is administered 1500 mg of durvalumab every four weeks.

In some embodiments, administration of an anti-PD-L1 antibody, like durvalumab, is administered in a fixed dose of 1500 mg and tremelimumab is administered as a fixed dose of 75 mg.

In some embodiments, administration of an anti-PD-L1 antibody, like durvalumab, is administered in a weight-based dose of 20 mg/kg and tremelimumab is administered as a weight-based dose of 1 mg/kg.

In some embodiments, a patient is administered intravenously a 1500 mg dose of durvalumab, optionally, a 75 mg dose of tremelimumab, a 80-100 mg/mL dose of etoposide, and either a carboplatin AUC dose of 5-6 mg/mL/min or a 75-80 mg/m² dose of cisplatin, Q3W.

In certain aspects, administration of therapeutic agents disclosed herein is via parenteral administration. For example, durvalumab or an antigen-binding fragment thereof and EP can be administered by intravenous infusion or by subcutaneous injection. In some aspects, the administration is by intravenous infusion.

In certain aspects, durvalumab or an antigen-binding fragment thereof and EP are administered according to the methods provided herein in combination or in conjunction with additional cancer therapies. Such therapies include, without limitation, chemotherapeutic agents such as Vemurafenib, Erlotinib, Afatinib, Cetuximab, Bevacizumab, Erlotinib, or Pemetrexed, or other chemotherapeutic agents, as well radiation or any other anti-cancer treatments.

The methods provided herein may provide for additional clinical benefits beyond those specifically identified and illustrated by the data including, for example, decreased tumor size, retardation of tumor growth, or maintenance of a steady state. In certain aspects, the reduction in tumor size can be significant based on appropriate statistical analyses. A reduction in tumor size can be measured by comparison to the size of patient's tumor at baseline, against an expected tumor size, against an expected tumor size based on a large patient population, or against the tumor size of a control population. In certain aspects provided herein, the administration of durvalumab with etoposide and cisplatin and/or carboplatin can reduce a tumor size by at least 25%, at least 50%, or at least 75%.

The methods provided herein can decrease or retard tumor growth. In some aspects the reduction or retardation can be statistically significant. A reduction in tumor growth can be measured by comparison to the growth of patient's tumor at baseline, against an expected tumor growth, against an expected tumor growth based on a large patient population, or against the tumor growth of a control population.

According to the methods provided herein, administration of an anti-PD-L1 antibody, for example, durvalumab or an antigen-binding fragment thereof, can result in desirable pharmacokinetic parameters. Total drug exposure can be estimated using the "area under the curve" (AUC). "AUC (tau)" refers to AUC until the end of the dosing period, whereas "AUC (inf)" refers to the AUC until infinite time. The administration can produce AUC (tau) of about 100 to about 2,500 d·1-g/mL. The administration can produce a maximum observed concentration (Cmax) of about 15 to about 350 1-g/mL. The half-life of the durvalumab or the antigen-binding fragment thereof can be about 5 to about 25 days. In addition, the clearance of the durvalumab or the antigen-binding fragment thereof can be about 1-10 mL/day/kg.

As provided herein, durvalumab or an antigen-binding fragment thereof can also decrease free PD-L1 levels. Free PD-L1 refers to PD-L1 that is not bound (e.g., by durvalumab). In some aspects, PD-L1 levels are reduced by at least 80%. In some aspects, PD-L1 levels are reduced by at least 90%. In some aspects, PD-L1 levels are reduced by at least 95%. In some aspects, PD-L1 levels are reduced by at least 99%. In some aspects, PD-L1 levels are eliminated following administration of durvalumab or an antigen-binding fragment thereof. In some aspects, administration of durvalumab or an antigen-binding fragment thereof reduces the rate of increase of PD-L1 levels as compared, e.g., to the rate of increase of PD-L1 levels prior to the administration of durvalumab or an antigen-binding fragment thereof.

The practice of the methods disclosed herein employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991).

The following examples provide an illustration of some of the aspects and aspects described above, and are not intended to limit the scope of the claimed invention.

EXAMPLES

Example 1

Clinical Assessment of Durvalumab, with or without Tremelimumab, in Combination with EP for the First-Line Treatment of Patients with ES-SCLC Most patients with SCLC have extensive-stage (ES) disease at diagnosis, with poor prognosis. Recently, immunotherapy has demonstrated clinical activity in ES-SCLC. This example provides results from a phase 3, randomized, open-label, sponsor-blind trial (CASPIAN, ClinicalTrials-.gov number NCT03043872) evaluating the efficacy and safety of durvalumab, with or without tremelimumab, in combination with EP for the first-line treatment of patients with ES-SCLC.

Patients

Eligible patients included adults with histologically or cytologically documented ES-SCLC and were treatment naïve. Patients also had a World Health Organization (WHO) performance-status score of 0 or 1, measurable disease according to RECIST v1.1, and a life expectancy of ≥12 weeks from the study start. Patients with brain metastases were eligible provided they were asymptomatic or treated and stable off steroids and anticonvulsants for at least 1 month prior to study entry.

Key exclusion criteria included history of radiotherapy to the chest or planned consolidation chest radiotherapy; active or previous autoimmune or inflammatory disorders; paraneoplastic syndrome of autoimmune nature requiring systemic treatment; history of active primary immunodeficiency; uncontrolled, concurrent illness or active infections.

Design and Treatments

Patients were randomized in a 1:1:1 ratio to receive durvalumab 1500 mg plus EP, durvalumab 1500 mg plus tremelimumab 75 mg plus EP, or EP (FIG. 1). Across all three study arms, chemotherapy consisted of etoposide 80-100 mg/m$^2$ (administered on days 1 to 3 of each cycle), with either carboplatin area under the curve 5-6 mg/mL/min or cisplatin 75-80 mg/m$^2$ (administered on day 1 of each cycle). Randomization was stratified according to planned platinum agent. Patients in the immunotherapy arms received up to 4 cycles of EP plus durvalumab every 3 weeks (q3w) followed by maintenance durvalumab 1500 mg every 4 weeks (q4w). Patients in the EP arm could receive an additional 2 cycles of EP (up to 6 cycles total) and prophylactic cranial irradiation (PCI). Patients continued treatment until Response Evaluation Criteria in Solid Tumor version 1.1 (RECIST v1.1)-defined disease progression, unacceptable toxicity, or other discontinuation criteria were met. Continuation of study treatment following disease progression was permitted if there was evidence of clinical benefit (FIG. 1). In-study crossover from the EP to the immunotherapy plus EP arms was not allowed. The general dosing scheme is shown in Table 1.

TABLE 1

Dosing Scheme.

| Treatment Arms | During Chemotherapy Q3W | | | | Post chemotherapy Q4W | | |
|---|---|---|---|---|---|---|---|
| | Cycle 1 Week 0 | Cycle 2 Week 3 | Cycle 3 Week 6 | Cycle 4 Week 9 | Week 12 | Week 16 | Week 20 to PD |
| Arm 1 | EP + Durva + Treme | EP + Durva + Treme | EP + Durva + Treme | EP + Durva + Treme | Durva | Durva + Treme* | Durva |
| Arm 2 | EP + Durva | EP + Durva | EP + Durva | EP + Durva | Durva | Durva | Durva |
| Arm3 | EP | EP | EP | EP** | | | |

*In the case of dose delay(s), more than one durvalumab + tremelimumab combination dose could be given post chemotherapy to ensure that up to 5 comination doses were administered in Arm 1.
**In Arm 3, EP could be given for an additional 2 cycles q3w on Weeks 12 and 15 (i.e., total 6 cycles post-randomization) if clinically indicated before patients enter Follow-up. PCI can also be given. This does not alter the planned scan schedule q8w starting at Week 12 for patients in Arm 3. Durvalumab dose will be 1500 mg during chemotherapy and post-chemotherapy; tremelimumab dose will be 75 mg during and post chemotherapy.
NOTE:
Patients whose weight falls to 30 kg or below received weight-based dosing equivalent to 20 mg/kg of durvalumab and 1 mg/kg tremelimumab until weight improved to >30 kg, at which point the patient started receiving the fixed dosing of durvalumab 1500 mg and 75 mg of tremelimumab.
EP, Etoposide and platinum-based chemotherapy;
Durva, Durvalumab;
PD Progessive disease;
Treme Tremelimumab;
q3w, Every 3 weeks;
q4w, Every 4 weeks.

Endpoints and Assessments

Tumor imaging was performed every 6 weeks for the first 12 weeks, and every 8 weeks thereafter, until confirmed objective disease progression. Survival was assessed every 2 months following treatment discontinuation. Adverse events (AEs) were graded according to National Cancer Institute Common Terminology Criteria for Adverse Events version 4.03.

The primary endpoint was OS (time from randomization to death from any cause). Secondary endpoints included progression-free survival (PFS; time from randomization to the date of objective disease progression or death from any cause in the absence of progression), objective response rate (ORR), OS at 18 and 24 months, PFS at 6 and 12 months, and safety. PFS and ORR were assessed according to RECIST v1.1.

Statistical Analysis

Figure 2:
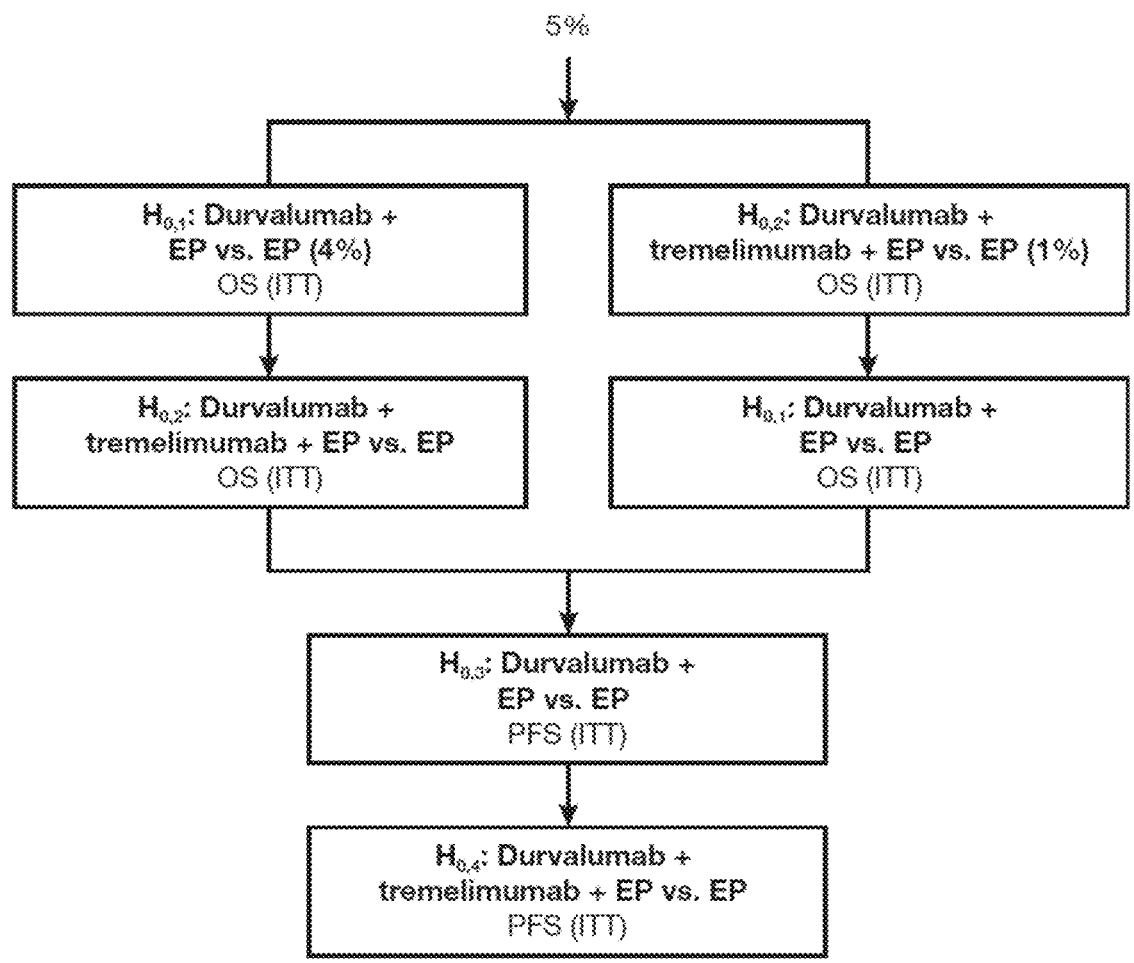
FIG. 2 shows hierarchical multiple testing procedure with a gatekeeping strategy that was used to control the type I error at a two-sided 5% significance level in the present disclosure. The hypotheses were to be tested using a multiple testing procedure with an alpha-exhaustive recycling strategy (Burman et al. A recycling framework for the construction of Bonferroni-based multiple tests. Stat Med 2009; 28:739-61). This strategy was used to test the two primary analyses of OS and two secondary analyses of PFS. PFS was therefore only to be tested within the multiple testing procedure if both OS primary analyses achieved significance. The overall 5% alpha was split between the primary endpoints: an alpha level of 4% was allocated to the analysis of OS for durvalumab plus EP versus EP, and an alpha level of 1% for the analysis of OS for durvalumab plus tremelimumab plus EP versus EP. EP, platinum-etoposide; H, hypothesis; ITT, intention-to-treat; OS, overall survival; PFS, progression-free survival.

The study was to be considered positive if OS was significantly longer with durvalumab plus EP or durvalumab plus tremelimumab plus EP versus EP alone. To control the type I error at 5% (two-sided), a hierarchical multiple testing procedure with a gatekeeping strategy was used across the primary OS analyses and secondary PFS analyses (FIG. 2). A 4% and 1% alpha were allocated to the primary endpoints of OS for durvalumab plus EP versus EP and OS for durvalumab plus tremelimumab plus EP versus EP, respectively. PFS was only to be formally tested within the multiple testing procedure if both OS primary analyses were significant.

Approximately 795 patients were needed for 1:1:1 randomization to obtain 425 events across the durvalumab plus EP and EP arms and 425 events across the durvalumab plus tremelimumab plus EP and EP arms (80% maturity) for the final analysis of OS. Sample size assumptions are detailed in Table 2.

TABLE 2

Sample size assumptions.

| Primary Endpoint | Power (%) | HR | Events | Overall 2-sided Significance Level (%) |
| --- | --- | --- | --- | --- |
| OS (durvalumab plus EP vs. EP) | 96 | 0.69 | 425 | 4* |
| OS (durvalumab plus tremelimumab plus EP vs. EP) | 89 | 0.69 | 425 | 1* |

*Adjusting for one interim analysis of OS planned when 75% of target OS events had occurred and final analysis of OS, using the Lan-DeMets spending function that approximates an O'Brien-Fleming approach to account for multiple comparisons (Lan K-KG et al. Discrete sequential boundaries for clinical trials. Biometrika 1983; 70: 659-63). EP, platinum-etoposide; HR, hazard ratio; OS, overall survival.

Efficacy data were analyzed on an intention-to-treat basis including all randomized patients, regardless of whether the treatment was actually received. All patients who received at least one dose of study treatment were included in safety analyses. OS and PFS were analyzed using a stratified log-rank test adjusting for planned platinum agent (carboplatin or cisplatin), with HRs and 95% confidence intervals (CI) estimated using a Cox proportional hazards model. The Kaplan-Meier method was used to estimate survival curves for OS and PFS. Sensitivity analyses for OS included examination of censoring patterns to rule out attrition bias. Sensitivity analyses for PFS included assessment of attrition bias and evaluation-time bias. Odds ratios and 95% CIs for comparing ORR between treatment arms were calculated using a logistic regression model, adjusted for planned platinum agent.

Results
Patients and Treatments

During the study 972 patients were screened, of whom 167 were excluded and 805 were randomly assigned to D+T+EP (n=268), D+EP (n=268), and EP alone (n=269). Baseline demographics were generally well balanced across groups (Table 3). Across all groups, the median age was 63 years (IQR 57-68) and most patients were men (576 [72%] of 805), current or former smokers (753 [94%]), and had stage IV disease at diagnosis (735 [91%]). Numerically, more patients had a WHO performance status score of 0, were male, had brain or CNS metastases, and had liver metastases at baseline in the D+T+EP group compared with the D+EP and the EP groups.

TABLE 3

Baseline Patient Demographics and Disease Characteristics.*

| | Durvalumab plus tremelimumab plus EP (n = 268) | Durvalumab plus EP (n = 268) | EP (n = 269) |
| --- | --- | --- | --- |
| Median age, years | 63 (58-68) | 62 (58-68) | 63 (57-68) |
| Age group, years | | | |
| <65 | 154 (57%) | 167 (62%) | 157 (58%) |
| ≥65 | 114 (43%) | 101 (38%) | 112 (42%) |
| Sex | | | |
| Men | 202 (75%) | 190 (71%) | 184 (68%) |
| Women | 66 (25%) | 78 (29%) | 85 (32%) |
| Race | | | |
| White | 215 (80%) | 229 (85%) | 221 (82%) |
| Asian | 47 (18%) | 36 (13%) | 42 (16%) |
| Black or African American | 1 (<1%) | 2 (1%) | 3 (1%) |
| Other or missing | 5 (2%) | 1 (<1%) | 3 (1%) |
| Disease stage* | | | |
| III | 18 (7%) | 28 (10%) | 24 (9%) |
| IV | 250 (93%) | 240 (90%) | 245 (91%) |
| WHO performance status | | | |
| 0 | 109 (41%) | 99 (37%) | 90 (33%) |
| 1 | 159 (59%) | 169 (63%) | 179 (67%) |
| Smoking history | | | |
| Never smoker | 15 (6%) | 22 (8%) | 15 (6%) |
| Former smoker | 141 (53%) | 126 (47%) | 128 (48%) |
| Current smoker | 112 (42%) | 120 (45%) | 126 (47%) |
| Brain or CNS metastases | | | |
| Yes | 38 (14%) | 28 (10%) | 27 (10%) |
| No | 230 (86%) | 240 (90%) | 242 (90%) |
| Liver metastases | | | |
| Yes | 117 (44%) | 108 (40%) | 104 (39%) |
| No | 151 (56%) | 160 (60%) | 165 (61%) |

Data are median (IQR) or n (%). EP = etoposide plus either cisplatin or carboplatin.
*All patients were confirmed as having extensive-stage small-cell lung cancer Of the 795 patients who received chemotherapy, 618 (78%) received carboplatin and 198 (25%) received cisplatin. The median (IQR) total duration of treatment with chemotherapy was 12.3 (12.0-13.5), 12.1 (12.0-13.1), and 19.0 (12.6-20.3) weeks in the D+T+EP, D+EP, and EP groups, respectively (Table 4). More than 80% of patients in each treatment group received at least four cycles of chemotherapy. Patients in the D+T+EP group had reduced exposure to durvalumab compared with patients in the D+EP group (Table 4). The median (IQR) total duration of treatment with durvalumab was 23.1 (14.1-38.3) weeks in the D+T+EP group and 28.0 (20.0-43.9) weeks in the D+EP group. The median (IQR) number of durvalumab doses was 6 (4-10) in the D+T+EP group and 7 (6-11) in the D+EP group. 161 (61%) of 266 treated patients in the D+T+EP group received the planned five doses of tremelimumab (Table 4).

TABLE 4

Chemotherapy regimen and duration of treatment (safety population)

|  | Durvalumab plus tremelimumab plus EP | Durvalumab plus EP | EP |
|---|---|---|---|
| Immunotherapy | (n = 266) | (n = 265) | (n = 266) |
| Median number of durvalumab doses | 6 (4-10) | 7 (6-11) | — |
| Patients receiving 12 or more durvalumab doses | 56 (21%) | 66 (25%) | — |
| Median total duration of durvalumab, weeks | 23.1 (14.1-38.3) | 28.0 (20.0-43.9) | — |
| Median number of tremelimumab doses | 5 (4-5) | — | — |
| Patients receiving five tremelimumab doses | 161 (61%) | — | — |
| Median total duration of tremelimumab, weeks | 20.0 (12.1-21.3) | — | — |
| Chemotherapy | (n = 264*) | (n = 265) | (n = 266) |
| Platinum received[†] | | | |
| Caboplatin | 202 (77%) | 208 (78%) | 208 (78%) |
| Cisplatin | 66 (25%) | 65 (25%) | 67 (25%) |
| Median number of cycles of EP[‡] | 4 (4-4) | 4 (4-4) | 6 (4-6) |
| Patients receiving four or more cycles of EP[‡] | 215 (81%) | 230 (87%) | 225 (85%) |
| Patients receiving five or more cycles of EP[‡] | 1 (<1%) | 3 (1%) | 167 (63%) |
| Patients receiving six cycles of EP[‡] | 1 (<1%) | 1 (<1%) | 151 (57%) |
| Median total duration of EP, weeks[‡] | 12.3 (12.0-13.5) | 12.1 (12.0-13.1) | 19.0 (12.6-20.3) |

Efficacy

Figure 6A:
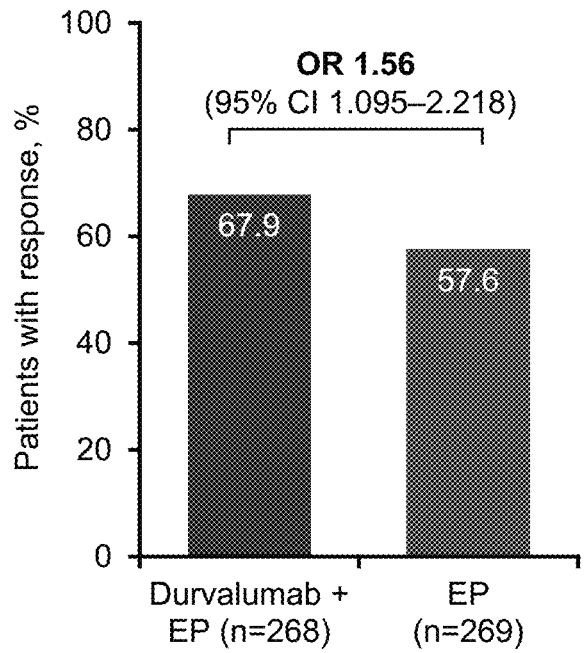
FIGS. 6A-6B show confirmed objective response.
Figure 6B:
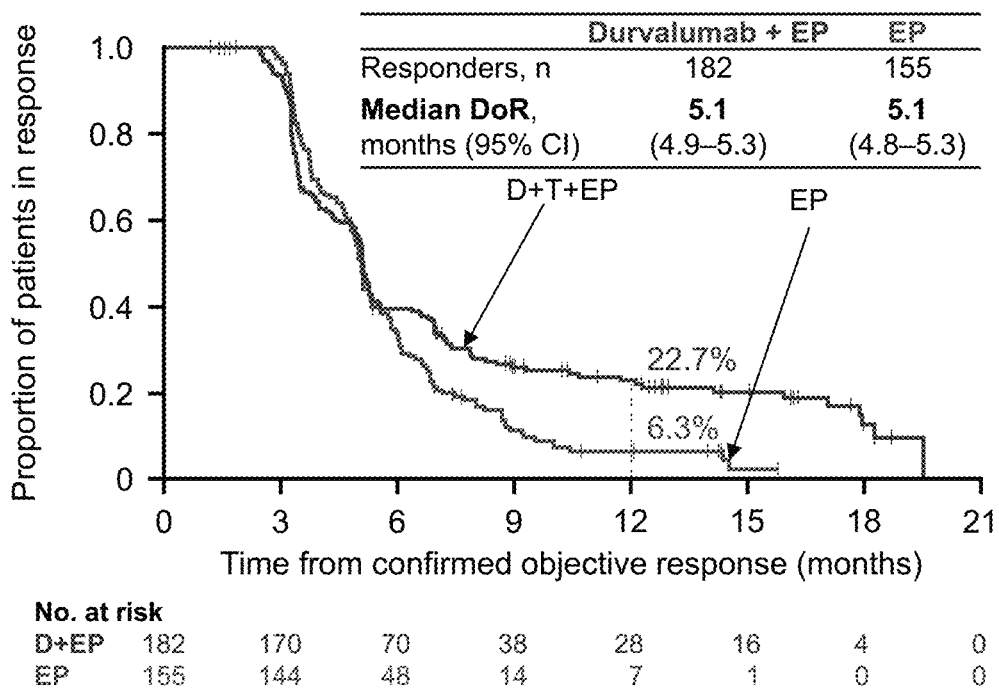

At interim analysis, confirmed ORR was higher with durvalumab plus EP versus EP (67.9% vs. 57.6%; odds ratio, 1.56; 95% CI, 1.095-2.218) (FIGS. 6A-6B and Table 5). Six (2.2%) patients treated with durvalumab plus EP and 2 (0.7%) patients treated with EP achieved a confirmed complete response. The median duration of response was 5.1 months for patients treated with both durvalumab plus EP and EP. Of those patients with a response, the proportion remaining in response at 12 months was higher with durvalumab plus EP versus EP (22.7% vs. 6.3%1.

TABLE 5

Overall responses at Interim Analysis

|  | Durvalumab + EP (n = 268) | EP (n = 269) |
|---|---|---|
| ORR, n (%)* | 182 (67.9) | 155 (57.6) |
| Odds ratio (95% CI)[†] | 1.56 (1.095-2.218) | — |
| Best objective response, n (%) | | |
| Complete response | 6 (2.2) | 2 (0.7) |
| Partial response | 176 (65.7) | 153 (56.9) |
| Stable disease ≥6 weeks | 20 (7.5) | 42 (15.6) |
| Progressive disease | 32 (11.9) | 31 (11.5) |
| Not evaluable | 3 (1.1) | 8 (3.0) |
| Median DoR, months (95% CI) | 5.1 (4.9-5.3) | 5.1 (4.8-5.3) |

TABLE 5-continued

Overall responses at Interim Analysis

|  | Durvalumab + EP (n = 268) | EP (n = 269) |
|---|---|---|
| Remaining in response, % | | |
| 6 months | 39.3 | 34.0 |
| 12 months | 22.7 | 6.3 |

*ORR per RECIST v1.1 is defined as the number (%) of patients with at least one visit response of complete response or partial response. Data included is for confirmed responses. [†]Odds ratios and 95% CIs for comparing ORR between treatment arms were calculated using a logistic regression model, adjusted for planned platinum agent (carboplatin or cisplatin).

As of data cutoff, the median duration of follow-up for OS in censored patients was 25.1 months (IQR 22.3-27.9) 30 (11%) of 268 patients in the D+T+EP group and 32 (12%) of 268 patients in the D+EP group remained on durvalumab treatment. 117 (44%) of 268 patients in the D+T+EP group, 123 (46%) of 268 in the D+EP group, and 125 (46%) of 269 in the EP group received at least one subsequent systemic anticancer therapy, with nearly all receiving chemotherapy (Table 6). A small proportion of patients received subsequent immunotherapy: 3 (1%) in the D+T+EP group, 6 (2%) in the D+EP group, and 17 (6%) in the EP group. Numerically lower use of two or more subsequent lines of systemic anticancer therapy was observed in the D+T+EP group (31 [12%] patients) compared with the D+EP (51 [19%]) and EP (49 [18%]) groups. 22 (8%) of 269 patients in the EP group received PCI after chemotherapy. In addition, PCI use after discontinuation of study treatment was reported in 7 (3%) of 268 patients in the D+T+EP group.

TABLE 6

Subsequent anticancer therapy

|  | Durvalumab + tremelimumab + EP (n = 268) | Durvalumab + EP (n = 268) | EP (n = 269) |
|---|---|---|---|
| Patients who received study treatment, n (%) | 266 (99) | 265 (99) | 266 (99) |
| Patients ongoing study treatment | 30 (11) | 32 (12) | 0 |
| Patients receiving any subsequent therapy, n (%) | 117 (44) | 123 (46) | 125 (46) |

TABLE 6-continued

Subsequent anticancer therapy

|  | Durvalumab + tremelimumab + EP (n = 268) | Durvalumab + EP (n = 268) | EP (n = 269) |
| --- | --- | --- | --- |
| Chemotherapy | 115 (43) | 120 (45) | 118 (44) |
| Single agent | 54 (20) | 64 (24) | 72 (27) |
| Platinum doublet | 46 (17) | 59 (22) | 50 (19) |
| Other | 33 (12) | 30 (11) | 31 (12) |
| Immunotherapy | 3 (1) | 6 (2) | 17 (6) |
| Single agent | 1 (<1) | 1 (<1) | 5 (2) |
| Immunotherapy + immunotherapy | 0 | 2 (1) | 3 (1) |
| Immunotherapy + chemotherapy | 1 (<1) | 1 (<1) | 3 (1) |
| Immunotherapy + other | 1 (<1) | 0 | 0 |
| Investigational agent | 0 | 3 (1) | 7 (3) |
| Other systemic therapies | 5 (2) | 4 (1) | 5 (2) |
| Patients receiving ≥1 subsequent line of treatment, n (%) | 117 (44) | 123 (46) | 125 (46) |
| Patients receiving ≥2 subsequent lines of treatment, n (%) | 31 (12) | 51 (19) | 49 (18) |
| Patients receiving >2 subsequent lines of treatment, n (%) | 7 (3) | 16 (6) | 13 (5) |

Figure 3A:
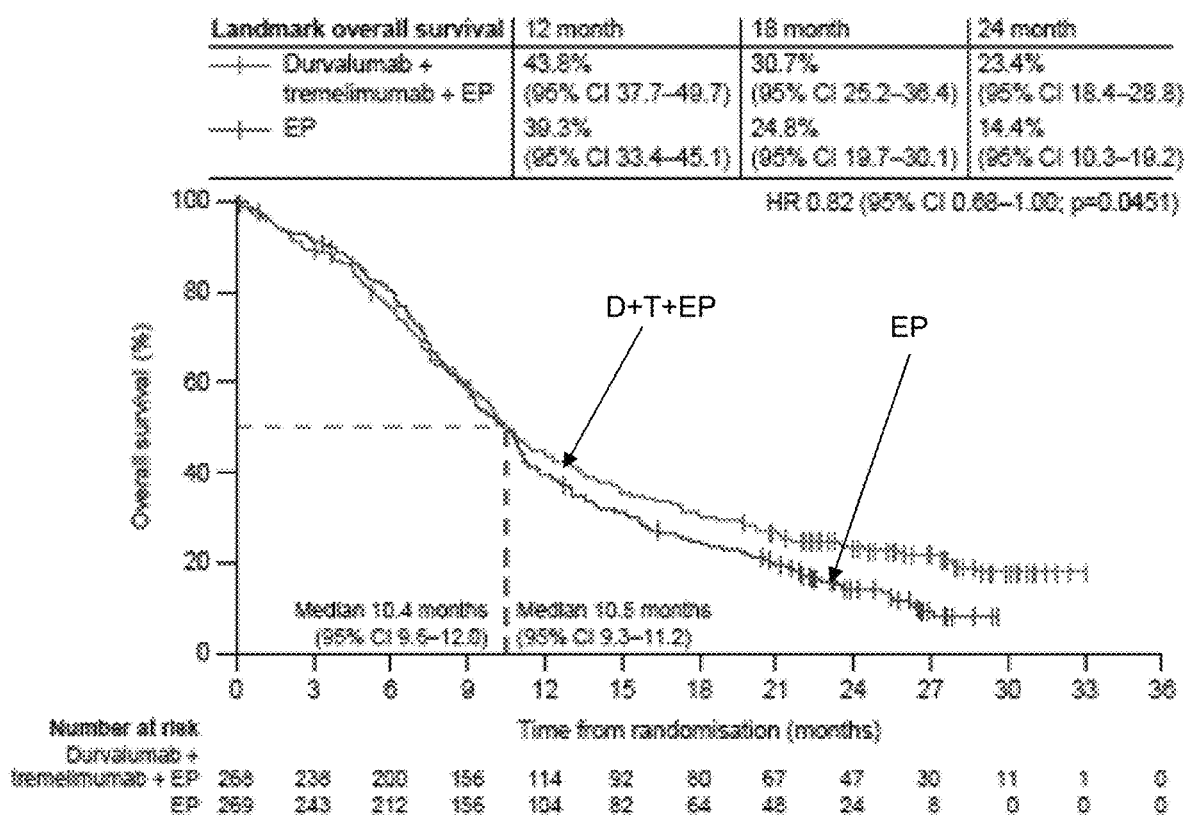
FIGS. 3A-3C show Overall survival in the intention-to-treat population. (3A) Kaplan-Meier graph for durvalumab plus tremelimumab plus EP versus EP; (3B) Kaplan-Meier graph for durvalumab plus EP versus EP; (3C) Subgroup analysis for durvalumab plus EP versus EP. CI, confidence interval; EP, platinum-etoposide; OS, overall survival; PFS, progression-free survival.

At the final analysis data cutoff, there were 438 deaths across the D+T+EP and EP groups (81.6% maturity); 207 (77%) patients in the D+T+EP group and 231 (86%) in the EP group had died. Based on the observed number of events at data cutoff, the multiplicity-adjusted, two-sided α spent at the final analysis of OS for D+T+EP versus EP was 4.18% (i.e., a p value less than 0.0418 was considered statistically significant). There was a numerical improvement in OS with D+T+EP versus EP; HR 0.82 (95% CI 0.68-1.00; p=0.0451; FIG. 3A). Median OS was 10.4 months (95% CI 9.6-12.0) with D+T+EP versus 10.5 months (9.3-11.2) with EP, 18-month OS rates were 30.7% (25.2-36.4) versus 24.8% (19.7-30.1), and 24-month OS rates were 23.4% (18.4-28.8) versus 14.4% (10.3-19.2).

Figure 4A:
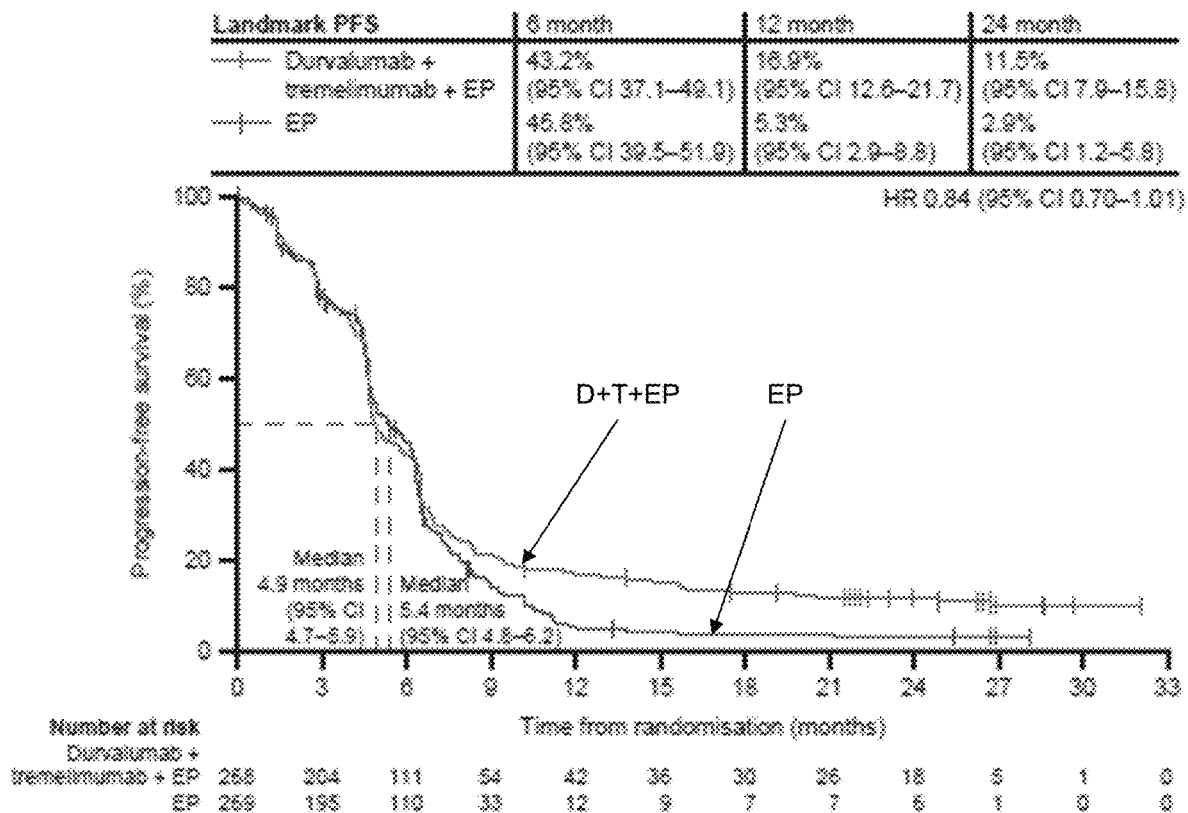
FIGS. 4A-4D show Progression-free survival and duration of response in the intention-to-treat population. (4A) Kaplan-Meier graph of progression-free survival for durvalumab plus tremelimumab plus EP versus EP; (4B) Kaplan-Meier graph of progression-free survival for durvalumab plus EP versus EP; (4C) Kaplan-Meier graph of duration of response for durvalumab plus tremelimumab plus EP versus EP; (4D) Kaplan-Meier graph of duration of response for durvalumab plus EP versus EP.

At the time of data cutoff, 229 (85%) of 268 patients in the D+T+EP group and 236 (88%) of 269 in the EP group had disease progression or died. The HR for PFS with D+T+EP versus EP was 0.84 (95% CI 0.70-1.01; FIG. 4A). Median PFS was 4.9 months (95% CI 4.7-5.9) with D+T+EP versus 5.4 months (4.8-6.2) with EP, 12-month PFS rates were 16.9% (12.6-21.7) versus 5.3% (2.9-8.8), and 24-month PFS rates were 11.5% (7.9-15.8) versus 2.9% (1.2-5.8).

Figure 4B:
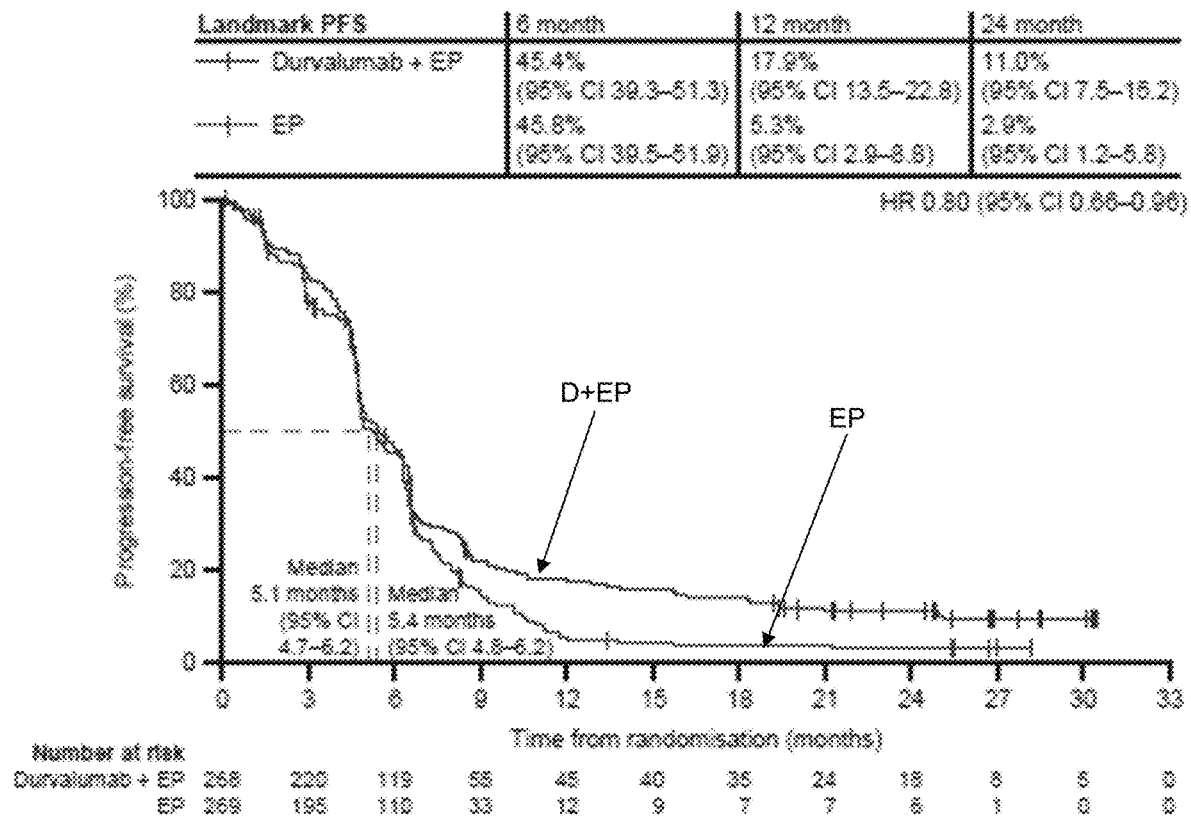
Figure 4C:
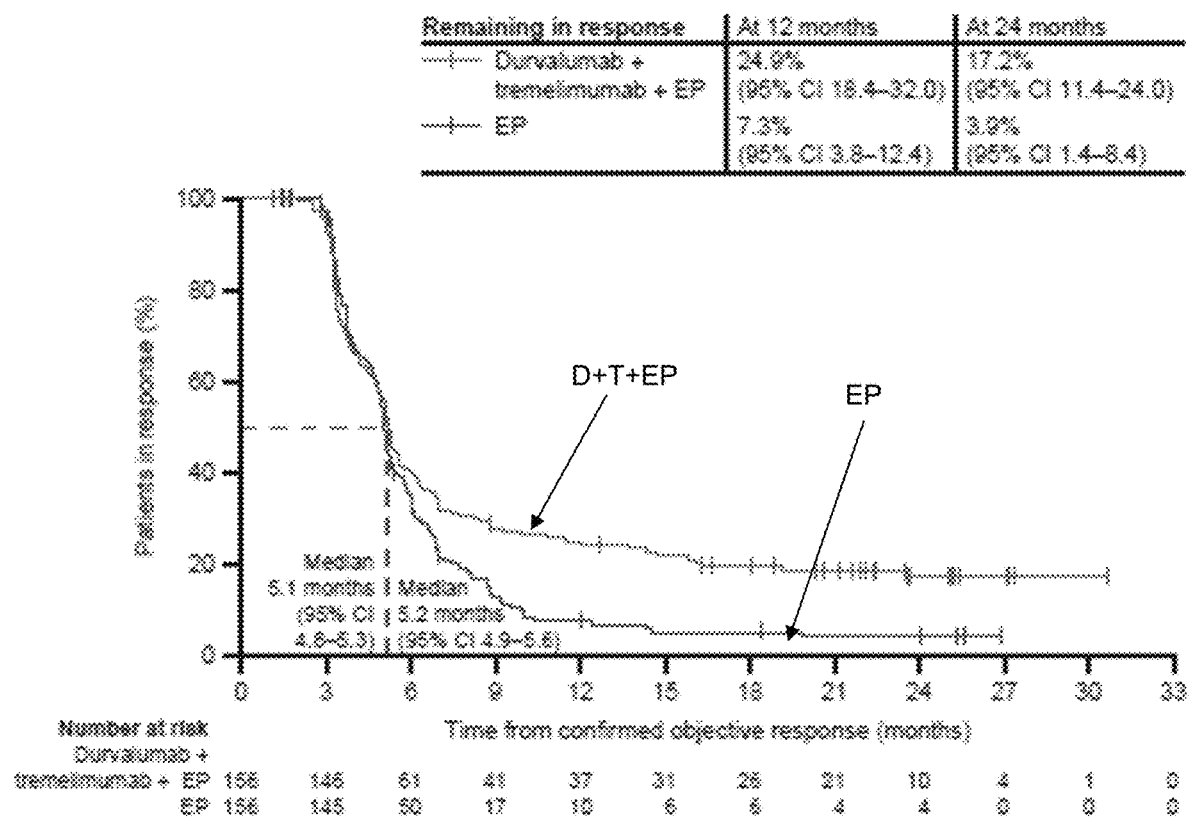
Figure 5A:
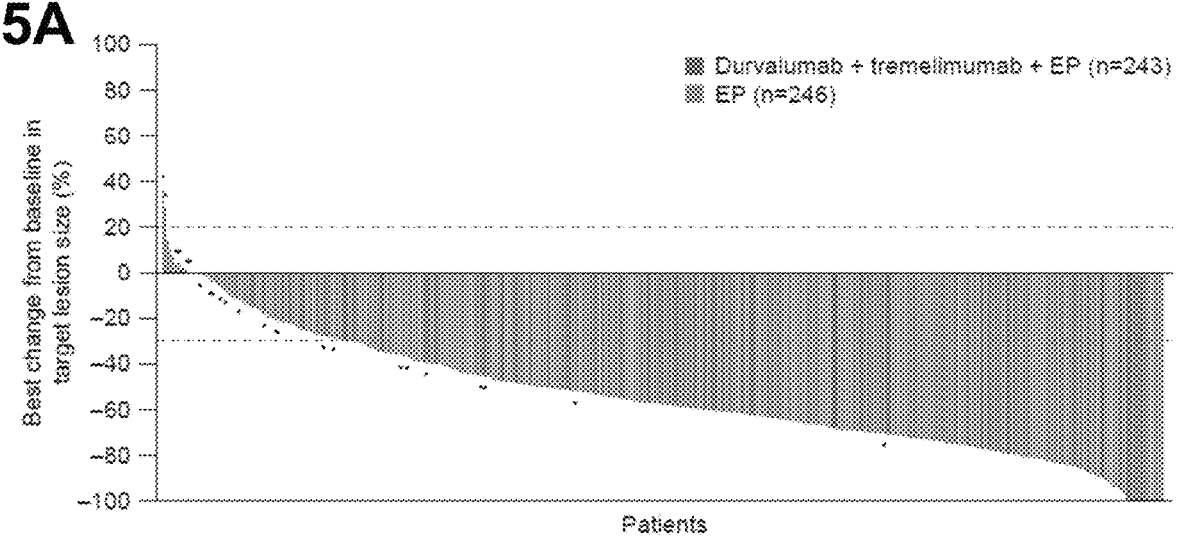
FIGS. 5A-5B show Best percentage change from baseline in target lesion size (5A) Durvalumab plus tremelimumab plus EP versus EP. (5B) Durvalumab plus EP versus EP.

The proportion of patients with an investigator-assessed unconfirmed objective response with D+T+EP (198 [74%] of 267 patients) versus EP (190 [71%] of 269 patients) was similar; odds ratio [OR] 1.19 (95% CI 0.82-1.75; Table 7). The proportion of patients with a confirmed objective response (analyzed post hoc) in the D+T+EP group (156 [58%] of 267 patients) was the same as in the EP group (156 [58%] of 269 patients); OR 1.02 (0.72-1.44). The median (IQR) best reduction from baseline in target lesion size was −59.3% (−73.6, 40.0) in the D+T+EP group compared with −55.9% (−71.3, 35.8) in the EP group. The depth of response is shown in FIG. 5A. Among patients with a confirmed response, the median duration of response was similar in the D+T+EP (5.2 months [95% CI 4.9-5.6]) and EP (5.1 months [4.8-5.3]) groups (FIG. 4C). The estimated percentage of patients remaining in response was higher with D+T+EP versus EP at both 12 (24.9% [18.4-3.0] vs 7.3% [3.8-12.4]) and 24 (17.2% [11.4-24.0] vs 3.9% [1.4-8.4]) months.

Figure 3B:
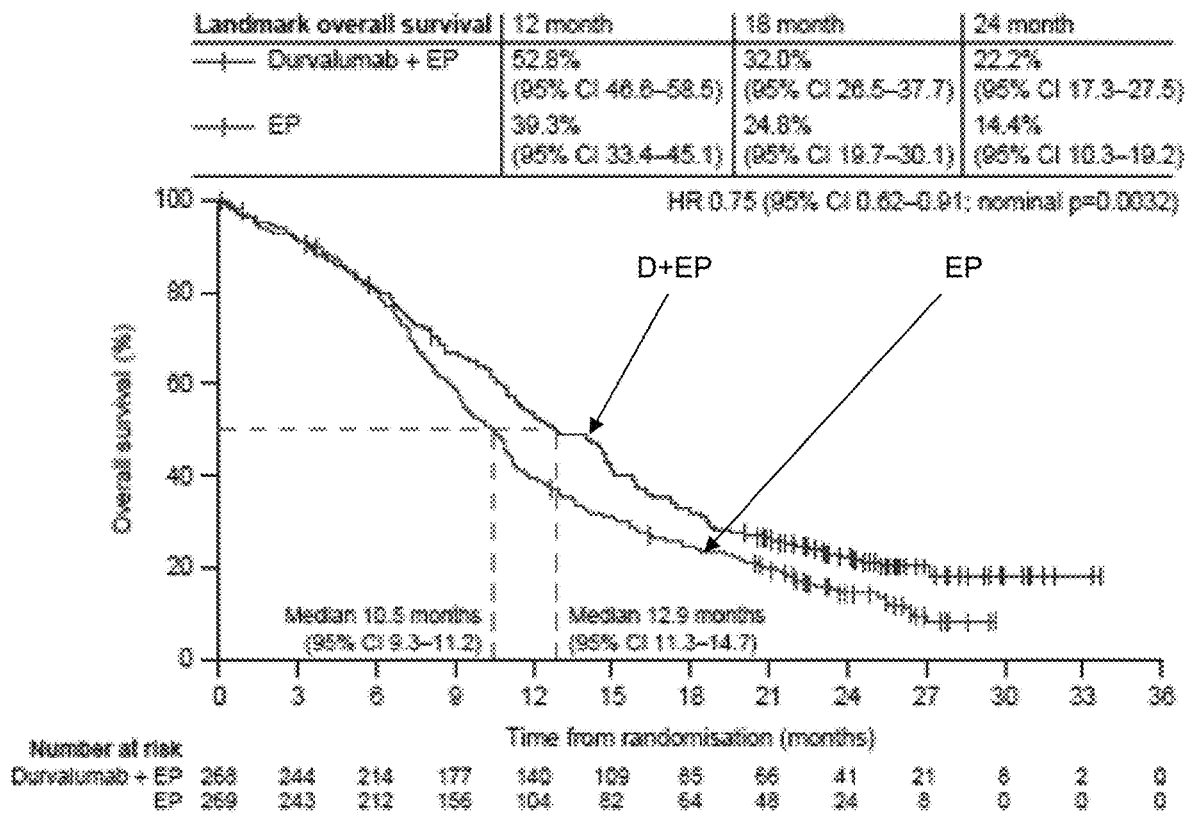
Figure 3C:
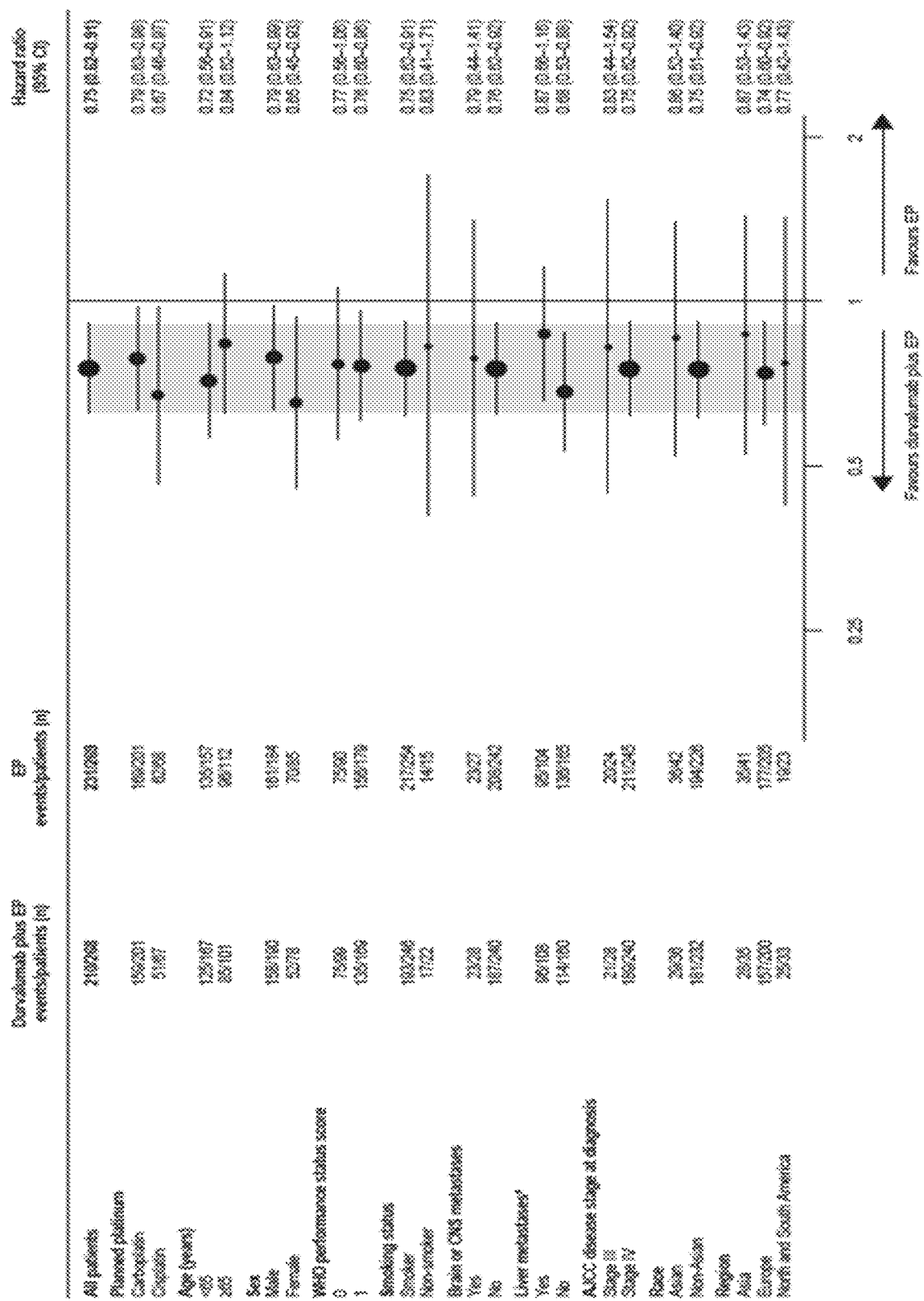

At the final analysis data cutoff, there were 441 deaths across the D+EP and EP groups (82.1% maturity); 210 (78%) patients in the D+EP group and 231 (86%) in the EP group had died. The OS benefit observed at the interim analysis for D+EP compared with EP was sustained with an additional 11 months of follow-up; in this updated analysis, the HR for OS was 0.75 (95% CI 0.62-0.91; nominal p=0.0032; FIG. 3B). Median OS was 12.9 months (95% CI 11.3-14.7) with D+EP and the 24-month OS rate was 22.2% (17.3-27.5). The HRs for OS consistently favored D+EP versus EP across all prespecified patient subgroups, as observed at the interim analysis, as well as post-hoc subgroups defined by liver metastases at baseline (FIG. 3C).

At the time of data cutoff, 234 (87%) of 268 patients in the D+EP group had disease progression or died. PFS favored D+EP versus EP, with an HR of 0.80 (95% CI 0.66-0.96; FIG. 4B). Median PFS was 5.1 months (95% CI 4.7-6.2) with D+EP and the 12-month and 24-month PFS rates were 17.9% (13.5-22.8) and 11.0% (7.5-15.2).

Figure 4D:
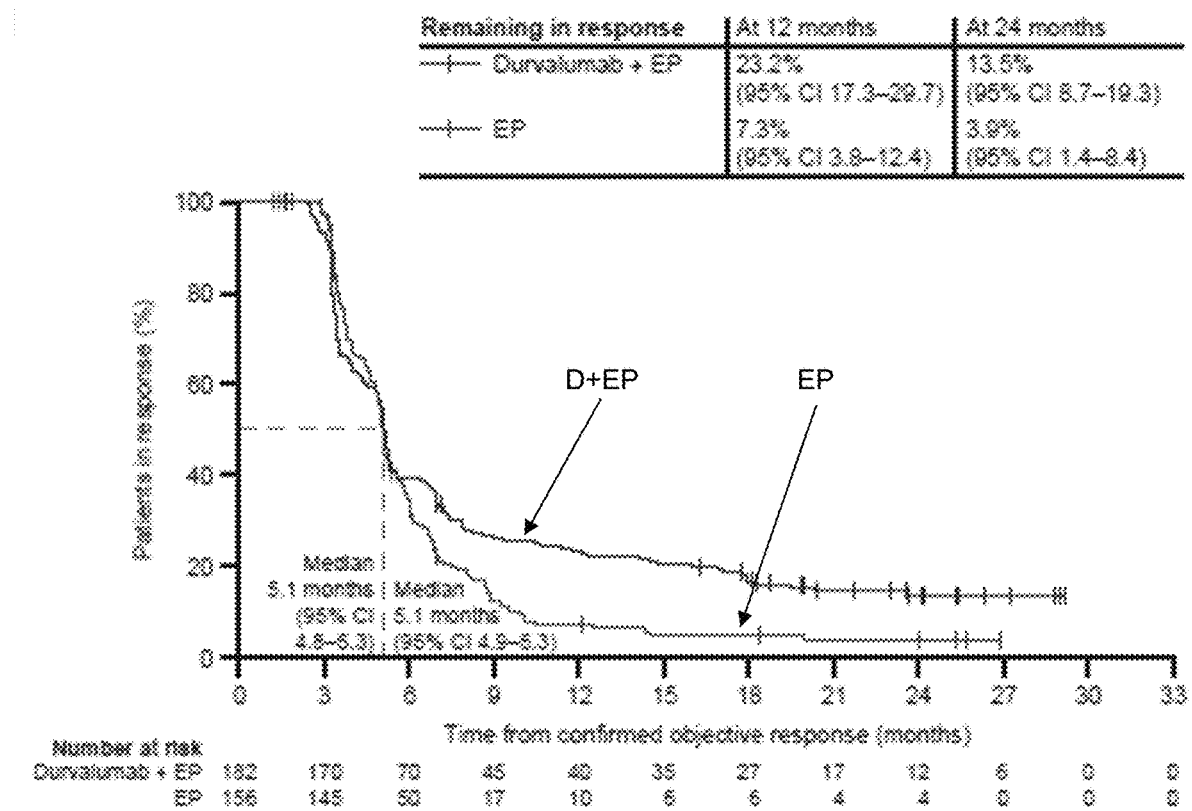
Figure 5B:
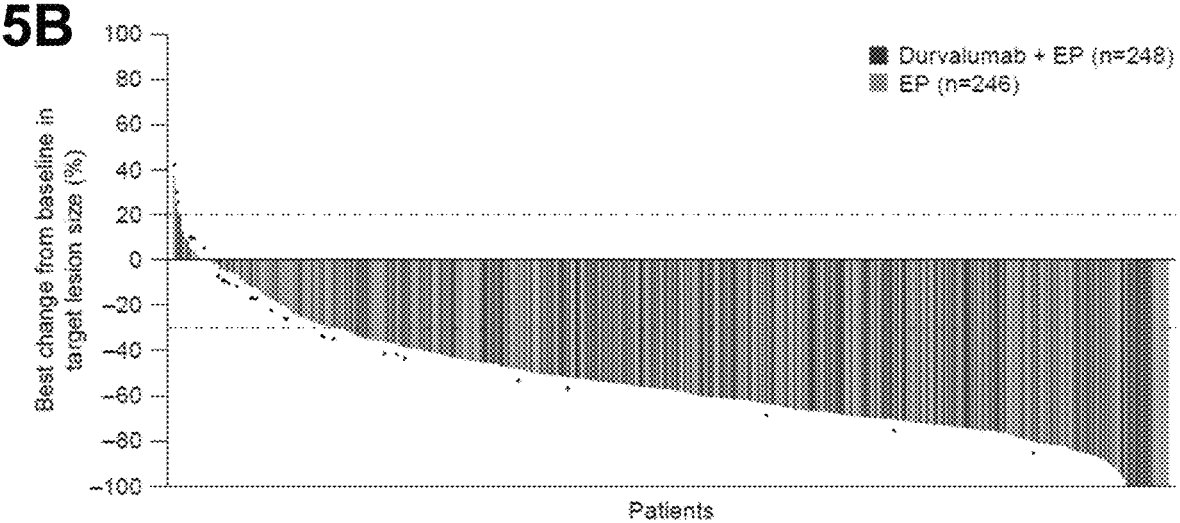

The proportion of patients with a confirmed objective response was higher with D+EP (182 [68%] of 268 patients) than with EP (58%); OR 1.53 (95% CI 1.08-2.18; Table 6). The median (IQR) best reduction from baseline in target lesion size was −60.4% (−72.9, −44.3) in the D+EP group. The depth of response is shown in FIG. 5B. Among patients with a confirmed response, the median duration of response was the same in the D+EP and EP groups (FIG. 4D). The proportion of patients remaining in response with D+EP at 12 and 24 months (23.2% [95% CI 17.3-29.7] and 13.5% [8.7-19.3]) was higher than in the EP group at both timepoints (7.3% and 3.9%; see above).

TABLE 7

Summary of tumor response.

|  | Durvalumab + tremelimumab + EP (n = 268) | Durvalumab + EP (n = 268) | EP (n = 269) |
| --- | --- | --- | --- |
| Unconfirmed objective response,* n/N[†] (%) | 198/267 (74) | 213/268 (79) | 190/269 (71) |
| Odds ratio vs EP (95% CI)[‡] | 1.19 (0.82-1.75) | 1.61 (1.09-2.40) | — |

TABLE 7-continued

Summary of tumor response.

|  | Durvalumab + tremelimumab + EP (n = 268) | Durvalumab + EP (n = 268) | EP (n = 269) |
|---|---|---|---|
| Confirmed objective response,* n/N† (%) | 156/267 (58) | 182/268 (68) | 156/269 (58) |
| Odds ratio vs EP (95% CI)‡ | 1.02 (0.72-1.44) | 1.53 (1.08-2.18) | — |
| Best objective response, n (%) |  |  |  |
| Complete response | 8 (3) | 7 (3) | 2 (1) |
| Partial response | 148 (55) | 175 (65) | 154 (57) |
| Stable disease for at least 6 weeks | 32 (12) | 20 (7) | 42 (16) |
| Unconfirmed response | 42 (16) | 31 (12) | 33 (12) |
| Progressive disease | 29 (11) | 32 (12) | 31 (12) |
| Not evaluable | 9 (3) | 3 (1) | 7 (3)§ |
| Best reduction from baseline in target lesion size, % |  |  |  |
| Median (IQR) | −59.3 (−73.6, −40.0) | −60.4 (−72.9, −44.3) | −55.9 (−71.3, −35.8) |
| Mean (SD) | −56.3 (25.10) | −57.0 (24.59) | −52.1 (26.20) |
| Median (95% CI) duration of response, months¶ | 5.2 (4.9-5.6) | 5.1 (4.9-5.3) | 5.1 (4.8-5.3) |
| Remaining in response, % (95% CI)¶ |  |  |  |
| 6 months | 40.2 (32.4-47.8) | 39.3 (32.2-46.3) | 34.7 (27.1-42.4) |
| 12 months | 24.9 (18.4-32.0) | 23.2 (17.3-29.7) | 7.3 (3.8-12.4) |
| 24 months | 17.2 (11.4-24.0) | 13.5 (8.7-19.3) | 3.9 (1.4-8.4) |

Data included are for confirmed responses except where otherwise specified. EP = etoposide plus either cisplatin or carboplatin.
*Objective response by investigator review per Response Evaluation Criteria in Solid Tumors, version 1.1, is defined as patients with complete response or partial response on at least one visit (unconfirmed responses); for confirmed responses, a confirmatory scan was required no sooner than 4 weeks after the initial response.
†N = patients with measurable disease at baseline
‡Odds ratios and 95% CIs were calculated using a logistic regression model adjusted for planned platinum (carboplatin or cisplatin); an odds ratio >1 favours immunotherapy.
§Includes one patient with an unconfirmed response (not evaluable due to no further assessments).
¶Estimated using the Kaplan-Meier method.

Safety

Treatment-related AEs, serious AEs and AEs leading to discontinuation are described in Table 8.

TABLE 8

Treatment-related adverse events (safety population)

|  | Durvalumab + tremelimumab + EP (n = 266) | | Durvalumab + EP (n = 265) | | EP (n = 266) | |
|---|---|---|---|---|---|---|
|  | Any grade | Grade 3 or 4 | Any grade | Grade 3 or 4 | Any grade | Grade 3 or 4 |
| Any treatment-related event, n (%) | 240 (90) | 147 (55) | 237 (89) | 121 (46) | 239 (90) | 138 (52) |
| Any treatment-related serious event, n (%) | 67 (25) | 55 (21) | 35 (13) | 25 (9) | 50 (19) | 45 (17) |
| Any treatment-related event leading to discontinuation, n (%)* | 43 (16) | 26 (10) | 16 (6) | 3 (1) | 13 (5) | 4 (2) |
| Any treatment-related event leading to death, n (%)† | 12 (5) | — | 6 (2) | — | 2 (1) | — |
| Treatment-related adverse events with an incidence of ≥5% in any grade category or events of grade 3 or 4 with an incidence of ≥2% in any group, n (%)‡ | | | | | | |
| Neutropenia | 110 (41) | 81 (30) | 104 (39) | 61 (23) | 116 (44) | 86 (32) |
| Anaemia | 84 (32) | 27 (10) | 85 (32) | 21 (8) | 103 (39) | 38 (14) |
| Alopecia | 72 (27) | 0 | 75 (28) | 3 (1) | 85 (32) | 2 (1) |
| Nausea | 66 (25) | 3 (1) | 74 (28) | 0 | 74 (28) | 5 (2) |
| Thrombocytopenia | 49 (18) | 22 (8) | 37 (14) | 14 (5) | 48 (18) | 24 (9) |
| Fatigue | 41 (15) | 2 (1) | 30 (11) | 2 (1) | 36 (14) | 3 (1) |
| Decreased appetite | 33 (12) | 2 (1) | 33 (12) | 1 (<1) | 35 (13) | 1 (<1) |
| Leucopenia | 31 (12) | 15 (6) | 36 (14) | 15 (6) | 32 (12) | 14 (5) |
| Vomiting | 25 (9) | 2 (1) | 32 (12) | 0 | 38 (14) | 2 (1) |
| Asthenia | 23 (9) | 3 (1) | 27 (10) | 2 (1) | 31 (12) | 2 (1) |
| Constipation | 25 (9) | 1 (<1) | 23 (9) | 0 | 24 (9) | 0 |
| Diarrhoea | 33 (12) | 7 (3) | 17 (6) | 2 (1) | 15 (6) | 2 (1) |

TABLE 8-continued

Treatment-related adverse events (safety population)

| | Durvalumab + tremelimumab + EP (n = 266) | | Durvalumab + EP (n = 265) | | EP (n = 266) | |
|---|---|---|---|---|---|---|
| | Any grade | Grade 3 or 4 | Any grade | Grade 3 or 4 | Any grade | Grade 3 or 4 |
| Neutrophil count decreased | 11 (4) | 11 (4) | 24 (9) | 16 (6) | 28 (11) | 17 (6) |
| Febrile neutropenia | 15 (6) | 12 (5) | 15 (6) | 13 (5) | 17 (6) | 17 (6) |
| Hyperthyroidism | 24 (9) | 1 (<1) | 22 (8) | 0 | 0 | 0 |
| Rash | 30 (11) | 3 (1) | 10 (4) | 0 | 6 (2) | 0 |
| Hypothyroidism | 22 (8) | 2 (1) | 23 (9) | 0 | 0 | 0 |
| Pruritus | 26 (10) | 0 | 11 (4) | 0 | 4 (2) | 0 |
| White blood cell count decreased | 9 (3) | 8 (3) | 12 (5) | 4 (2) | 17 (6) | 6 (2) |
| Paraesthesia | 9 (3) | 1 (<1) | 14 (5) | 0 | 11 (4) | 0 |
| Platelet count decreased | 6 (2) | 3 (1) | 14 (5) | 4 (2) | 13 (5) | 6 (2) |
| Lipase increased | 7 (3) | 5 (2) | 10 (4) | 8 (3) | 2 (1) | 1 (<1) |

Listed are all adverse events assessed by the investigator as possibly related to any study treatment that occurred during the treatment period and up to 90 days after the last dose of study treatment or up to the start of any subsequent therapy (whichever occurred first).
EP = etoposide plus either cisplatin or carboplatin
[†]Treatment-related adverse events leading to death were death, febrile neutropenia, and pulmonary embolism in two patients each, and enterocolitis, general physical health deterioration/multiple organ dysfunction syndrome, pneumonia, pneumonitis/hepatitis, respiratory failure, and sudden death in one patient each in the durvalumab plus tremelimumab plus EP group; cardiac arrest, dehydration, hepatotoxicity, interstitial lung disease, pancytopenia, and sepsis in one patient each in the durvalumab plus EP group; and pancytopenia and thrombocytopenia/hemorrhage in one patient each in the EP group.
[‡]The events are listed in descending order of frequency across all treatment groups.

Discussion

CASPIAN is the first pivotal trial to demonstrate a significant survival benefit with PD-1/PD-L1 blockade in combination with etoposide and a choice of carboplatin or cisplatin chemotherapy. This represents an important therapeutic advance given that in recent years (2014-2016) cisplatin-containing chemotherapy was used for 27-42% of patients in the first-line treatment of ES-SCLC in different regions globally (DiBonaventura M D, Shah-Manek B, Higginbottom K, Penrod J R, Yuan Y. Adherence to recommended clinical guidelines in extensive disease small-cell lung cancer across the US, Europe, and Japan. *Ther Clin Risk Manag* 2019; 15: 355-66).

D+EP met the primary endpoint of improved survival compared with EP alone at the planned interim analysis (Paz-Ares L, Dvorkin M, Chen Y, et al. Durvalumab plus platinum-etoposide versus platinum-etoposide in first-line treatment of extensive-stage small-cell lung cancer (CASPIAN): a randomised, controlled, open-label, phase 3 trial. *Lancet* 2019; 394: 1929-39). This updated analysis, with more than 2 years of median follow-up, demonstrated sustained OS improvement with D+EP. The proportion of patients alive was numerically higher with D+EP versus EP at all landmark timepoints; the 24-month OS rate was 22.2% with D+EP versus 14.4% with EP and the separation of the Kaplan-Meier curves was maintained to the end of follow-up. The OS benefit with D+EP versus EP was consistently demonstrated across all patient subgroups, including those treated with cisplatin and those with brain metastases at baseline. In the updated analysis, PFS remained in favor of D+EP versus EP with an HR of 0.80 (95% CI 0.66-0.96). PFS rates were numerically higher with D+EP versus EP at 12 (17.9% vs 5.3%) and 24 (11.0% vs 2.9%) months. Both the unconfirmed and confirmed objective response rates were approximately 10% higher with D+EP versus EP, consistent with the interim analysis. In addition, the proportion of patients remaining in response was greater with D+EP than with EP at both 12 (23.2% vs 7.3%) and 24 (13.5% vs 3.9%) months. After an additional year of follow-up, D+EP continued to demonstrate a manageable safety profile that was consistent with the interim analysis and the established safety profiles of the individual agents.

The tails of the OS Kaplan-Meier curves for both immunotherapy groups were similar, with more than 20% of patients alive at 24 months in each group. This suggests a consistent, durable benefit in patients with ES-SCLC with the addition of durvalumab to EP followed by maintenance durvalumab with convenient every-4-week dosing. The sustained benefit is particularly noteworthy in this aggressive disease setting where, historically, it has been difficult to demonstrate long-term survival benefit. Similarity between the immunotherapy groups was also seen in the tails of the PFS Kapan-Meier curves. The observation that nearly 20% of patients were progression free at 12 months across both durvalumab groups (compared with 5% in the EP group), and that many of these patients remained progression free even at 24 months, suggests that there is a proportion of patients with ES-SCLC who derive long-term clinical benefit with D+EP.

This is also the first report of a phase 3 trial evaluating dual immune checkpoint blockade in combination with chemotherapy in ES-SCLC. Although the median OS with D+T+EP compared with EP were similar, the Kaplan-Meier curve for the D+T+EP group started to separate from the EP curve after 10 months and, notably, the 24-month OS rate was 23.4% with D+T+EP versus 14.4% with EP. The HR for PFS was 0.84 for D+T+EP versus EP and the associated 95% CI crossed 1 (0.70-1.01). Similar to OS, there was late separation of the Kaplan-Meier curves and the 12-month and 24-month PFS rates were numerically higher with D+T+EP versus EP (16.9% vs 5.3% and 11.5% vs 2.9%, respectively). There was similarity between the D+T+EP and EP groups in the confirmed objective response rate or median duration of response. However, the proportion of patients remaining in response was greater with D+T+EP than with EP at both 12 and 24 months.

In conclusion, The results from this randomized, open-label, phase 3 trial demonstrate sustained OS benefit with the addition of durvalumab to EP in patients with ES-SCLC compared with a robust control group. Safety findings in all groups remained consistent with the known safety profiles of the individual drugs. These results support the use of D+EP as a new standard of care for the first-line treatment of ES-SCLC, offering the flexibility of platinum choice and an every-4-weeks maintenance dosing schedule that expands treatment options for patients and physicians.

Other Aspects

From the foregoing description, it will be apparent that variations and modifications may be made to the invention described herein to adopt it to various usages and conditions. Such aspects are also within the scope of the following claims.

The recitation of a listing of elements in any definition of a variable herein includes definitions of that variable as any single element or combination (or subcombination) of listed elements. The recitation of an aspect herein includes that aspect as any single aspect or in combination with any other aspects or portions thereof.

All patents and publications mentioned in this specification are herein incorporated by reference to the same extent as if each independent patent and publication was specifically and individually indicated to be incorporated by reference.

```
                       SEQUENCE LISTING

SEQ ID NO: 1
EIVLTQSPGTLSLSPGERATLSCRASQRVSSSYLAWYQQKPGQAPRLLIYD

ASSRATGIPDRFSGSGSGTDFTLTISRLEPEDFAVYYCQQYGSLPWTFGQG

TKVEIK

SEQ ID NO: 2
EVQLVESGGGLVQPGGSLRLSCAASGFTFSRYWMSWVRQAPGKGLEWVANI

KQDGSEKYYVDSVKGRFTISRDNAKNSLYLQMNSLRAEDTAVYYCAREGGW

FGELAFDYWGQGTLVTVSS

VH CDR1
                                                 SEQ ID NO: 3
GFTFSRYWMS

VH CDR2
                                                 SEQ ID NO: 4
NIKQDGSEKYYVDSVKG

VH CDR3
                                                 SEQ ID NO: 5
EGGWFGELAFDY

VL CDR1
                                                 SEQ ID NO: 6
RASQRVSSSYLA

VL CDR2
                                                 SEQ ID NO: 7
DASSRAT

VL CDR3
                                                 SEQ ID NO: 8
QQYGSLPWT
```

What is claimed is:

1. A method of extending progression-free survival (PFS) in a patient with extensive-stage small cell lung cancer (ES-SCLC), comprising:
   treating the patient with up to four cycles of
   i) a human anti-PD-L1 antibody, wherein the anti-PD-L1 antibody comprises durvalumab, and
   ii) an etoposide and a platinum-based therapeutic agent (EP);
   wherein the anti-PD-L1 antibody and EP are administered every three weeks (Q3W) followed by a maintenance phase wherein the anti-PD-L1 antibody is administered every four weeks (Q4W).

2. The method of claim 1, wherein the platinum-based therapeutic agent comprises cisplatin and/or carboplatin.

3. The method of claim 1, wherein the human anti-PD-L1 antibody comprises a light chain variable domain comprising the amino acid sequence of SEQ ID NO: 1 and a heavy chain variable domain comprising the amino acid sequence of SEQ ID NO: 2.

4. The method of claim 1, wherein the human anti-PD-L1 antibody comprises:
   a VH CDR1 having the amino acid sequence of SEQ ID NO: 3;
   a VH CDR2 having the amino acid sequence of SEQ ID NO: 4;
   a VH CDR3 having the amino acid sequence of SEQ ID NO: 5;
   a VL CDR1 having the amino acid sequence of SEQ ID NO: 6;
   a VL CDR2 having the amino acid sequence of SEQ ID NO: 7; and
   a VL CDR3 having the amino acid sequence of SEQ ID NO: 8.

5. The method of claim 1, wherein the human anti-PD-L1 antibody is administered as a fixed dose of 1500 mg.

6. The method of claim 1, wherein the human anti-PD-L1 antibody is administered as a dose of 20 mg/kg.

7. The method of claim 1, wherein EP is administered as a dose comprising 80-100 mg/m² etoposide and carboplatin area under the curve 5-6 mg/mL/min or cisplatin 75-80 mg/m², per dose of human anti-PD-L1 antibody.

8. The method of claim 1, wherein (i) further comprises administration of a human anti-CTLA-4 antibody, Q3W.

9. The method of claim 8, wherein the human anti-CTLA-4 antibody is tremelimumab.

10. The method of claim 9, wherein tremelimumab is administered as a fixed dose of 75 mg.

11. The method of claim 9, wherein tremelimumab is administered as a dose of 1 mg/kg.

12. The method of claim 1, further comprising administration of prophylactic cranial irradiation to the patient.

13. The method of claim 1, further comprising treating the patient with a human anti-PD-1 antibody.

14. The method of claim 13, wherein the human anti-PD-1 antibody comprises pembrolizumab-or nivolumab.

15. A method of extending overall survival (OS) in a patient with extensive-stage small cell lung cancer (ES-SCLC), comprising:
    treating the patient with up to four cycles of
        i) a human anti-PD-L1 antibody, wherein the anti-PD-L1 antibody comprises durvalumab, and
        ii) an etoposide and a platinum-based therapeutic agent (EP);
    wherein the anti-PD-L1 antibody and EP are administered every three weeks (Q3W) followed by a maintenance phase wherein the anti-PD-L1 antibody is administered every four weeks (Q4W)
    increase OS in the patient by at least about three months versus treatment with EP alone.

16. The method of claim 15, wherein the platinum-based therapeutic agent comprises cisplatin and/or carboplatin.

17. The method of claim 15, wherein the human anti-PD-L1 antibody comprises a light chain variable domain comprising the amino acid sequence of SEQ ID NO: 1 and a heavy chain variable domain comprising the amino acid sequence of SEQ ID NO: 2.

18. The method of claim 15, wherein the human anti-PD-L1 antibody comprises:
    a VH CDR1 having the amino acid sequence of SEQ ID NO: 3;
    a VH CDR2 having the amino acid sequence of SEQ ID NO: 4;
    a VH CDR3 having the amino acid sequence of SEQ ID NO: 5;
    a VL CDR1 having the amino acid sequence of SEQ ID NO: 6;
    a VL CDR2 having the amino acid sequence of SEQ ID NO: 7; and
    a VL CDR3 having the amino acid sequence of SEQ ID NO: 8.

19. The method of claim 15, wherein the human anti-PD-L1 antibody is administered as a fixed dose of 1500 mg.

20. The method of claim 15, wherein the human anti-PD-L1 antibody is administered as a dose of 20 mg/kg.

21. The method of claim 15, wherein EP is administered as a dose comprising 80-100 mg/m$^2$ etoposide and carboplatin area under the curve 5-6 mg/mL/min or cisplatin 75-80 mg/m$^2$, per dose of human anti-PD-L1 antibody.

22. The method of claim 15, wherein the maintenance phase comprises administration of 1500 mg human anti-PD-L1 antibody, Q4W after completion of 4 cycles of the anti-PD-L1 anitbody and EP (Q3W).

23. The method of claim 15, wherein (i) further comprises administration of a human anti-CTLA-4 antibody, Q3W.

24. The method of claim 23, wherein the human anti-CTLA-4 antibody is tremelimumab.

25. The method of claim 24, wherein tremelimumab is administered as a fixed dose of 75 mg.

26. The method of claim 24, wherein tremelimumab is administered as a dose of 1 mg/kg.

27. The method of claim 15, further comprising administration of prophylactic cranial irradiation to the patient.

28. The method of claim 15, further comprising treating the patient with a human anti-PD-1 antibody.

29. The method of claim 28, wherein the human anti-PD-1 antibody comprises pembrolizumab or nivolumab.

30. A method of improving overall response rate (ORR) in a patient with extensive-stage small cell lung cancer (ES-SCLC), comprising:
    treating the patient with up to four cycles of
        i) a human anti-PD-L1 antibody, wherein the anti-PD-L1 antibody comprises durvalumab, and
        ii) etoposide and a platinum-based therapeutic agent (EP); wherein the anti-PD-L1 antibody and EP are administered every three weeks (Q3W) followed by a maintenance phase wherein the anti-PD-L1 antibody is administered every four weeks (Q4W)
    increase ORR in the patient by at least 10% versus treatment with EP alone.

31. The method of claim 30, wherein the platinum-based therapeutic agent comprises cisplatin and/or carboplatin.

32. The method of claim 30, wherein the human anti-PD-L1 antibody comprises a light chain variable domain comprising the amino acid sequence of SEQ ID NO: 1 and a heavy chain variable domain comprising the amino acid sequence of SEQ ID NO: 2.

33. The method of claim 30, wherein the human anti-PD-L1 antibody comprises:
    a VH CDR1 having the amino acid sequence of SEQ ID NO: 3;
    a VH CDR2 having the amino acid sequence of SEQ ID NO: 4;
    a VH CDR3 having the amino acid sequence of SEQ ID NO: 5;
    a VL CDR1 having the amino acid sequence of SEQ ID NO: 6;
    a VL CDR2 having the amino acid sequence of SEQ ID NO: 7; and
    a VL CDR3 having the amino acid sequence of SEQ ID NO: 8.

34. The method of claim 30, wherein the human anti-PD-L1 antibody is durvalumab, avelumab, or atezolizumab.

35. The method of claim 30, wherein the human anti-PD-L1 antibody is administered as a fixed dose of 1500 mg.

36. The method of claim 30, wherein the human anti-PD-L1 antibody is administered as a dose of 20 mg/kg.

37. The method of either claim 35 or 36, wherein the method comprises 4 cycles of administration of the human anti-PD-L1 antibody.

38. The method of claim 30, wherein EP is administered as a dose comprising 80-100 mg/m$^2$ etoposide and carboplatin area under the curve 5-6 mg/mL/min or cisplatin 75-80 mg/m$^2$, intravenously, per dose of human anti-PD-L1 antibody.

39. The method of claim 30, wherein the maintenance phase comprises administration of 1500 mg human anti-PD-L1 antibody Q4W after completion of 4 cycles of the anti-PD-L1 antibody and EP every 3 weeks (Q3W).

40. The method of claim 30, wherein (i) further comprises administration of a human anti-CTLA-4 antibody Q3W.

41. The method of claim 40, wherein the human anti-CTLA-4 antibody is tremelimumab.

42. The method of claim 41, wherein tremelimumab is administered as a fixed dose of 75 mg.

43. The method of claim 41, wherein tremelimumab is administered as a dose of 1 mg/kg.

44. The method of claim 30, further comprising administration of prophylactic cranial irradiation to the patient.

45. The method of claim 30, further comprising treating the patient with a human anti-PD-1 antibody.

46. The method of claim 45, wherein the human anti-PD-1 antibody comprises pembrolizumab or nivolumab.

47. The method of claim 1, 15, or 30, wherein two additional cycles of the human anti-PD-L1 antibody and EP are administered every three weeks, prior to the maintenance phase.

48. The method of any one of the preceding claims, wherein the human anti-PD-L1 antibody and/or the human anti-CTLA-4 antibody are administered intravenously.

\* \* \* \* \*